United States Patent
Ooi et al.

(10) Patent No.: US 12,203,895 B2
(45) Date of Patent: Jan. 21, 2025

(54) SIGNAL PROCESSING ALGORITHM FOR DETECTING RED PALM WEEVILS USING OPTICAL FIBER

(71) Applicant: KING ABDULLAH UNIVERSITY OF SCIENCE AND TECHNOLOGY, Thuwal (SA)

(72) Inventors: Boon Siew Ooi, Thuwal (SA); Islam Ashry, Thuwal (SA); Yuan Mao, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 390 days.

(21) Appl. No.: 17/603,685

(22) PCT Filed: Apr. 20, 2020

(86) PCT No.: PCT/IB2020/053728
§ 371 (c)(1),
(2) Date: Oct. 14, 2021

(87) PCT Pub. No.: WO2020/217160
PCT Pub. Date: Oct. 29, 2020

(65) Prior Publication Data
US 2022/0299481 A1 Sep. 22, 2022

Related U.S. Application Data

(60) Provisional application No. 62/836,882, filed on Apr. 22, 2019.

(51) Int. Cl.
*G01N 29/24* (2006.01)
*G01D 5/353* (2006.01)
(Continued)

(52) U.S. Cl.
CPC ..... *G01N 29/2418* (2013.01); *G01D 5/35361* (2013.01); *G01H 9/006* (2013.01);
(Continued)

(58) Field of Classification Search
CPC .... G01N 29/2418; G01N 29/14; G01N 29/48; G01N 33/0098; G01N 2291/0238;
(Continued)

(56) References Cited

U.S. PATENT DOCUMENTS 9,736,597 B1 * 8/2017 Spiegelberg ......... H04R 23/008
10,345,138 B2 * 7/2019 Milione ............... G01H 9/004
(Continued)

FOREIGN PATENT DOCUMENTS

CN 1459037 A 11/2003
CN 101277150 A 10/2008
(Continued)

OTHER PUBLICATIONS

De la Rosa et al., Higher-order cumulants and spectral kurtosis for early detection of subterranean termites, Mechanical Systems and Signal Processing, Sep. 2007, p. 16 (Year: 2007).*
(Continued)

*Primary Examiner* — Stephanie E Bloss
*Assistant Examiner* — Kevin C Butler
(74) *Attorney, Agent, or Firm* — PATENT PORTFOLIO BUILDERS PLLC

(57) ABSTRACT

A method for determining tree infestation includes placing an optical fiber around a trunk of a tree; recording with a distributed acoustic sensor (DAS) box a Rayleigh signal reflected from the tree, along the optical fiber; processing the Rayleigh signal to obtain a processed signal; calculating a signal-to-noise ratio (SNR) of the processed signal for the tree; and comparing the SNR to a threshold value and counting an alarm if the SNR is larger than the threshold
(Continued)

value. The SNR is defined as a ratio between (1) a maximum value of a processed signal and (2) a minimum value of the processed signal.

20 Claims, 23 Drawing Sheets

(51) Int. Cl.
  *G01H 9/00* (2006.01)
  *G01N 29/14* (2006.01)
  *G01N 29/48* (2006.01)
  *G01N 33/00* (2006.01)
  *H04B 10/071* (2013.01)

(52) U.S. Cl.
  CPC ............ *G01N 29/14* (2013.01); *G01N 29/48* (2013.01); *G01N 33/0098* (2013.01); *H04B 10/071* (2013.01); *G01N 2291/0238* (2013.01)

(58) Field of Classification Search
  CPC ....... G01N 2291/0423; G01D 5/35361; G01H 9/006; G01H 9/00; G01H 9/004; G01H 1/006; H04B 10/071
  USPC ......................................................... 73/655
  See application file for complete search history.

(56) References Cited

U.S. PATENT DOCUMENTS

| | | | |
|---|---|---|---|
| 2017/0211970 A1 | 7/2017 | Milione et al. | |
| 2017/0238101 A1 | 8/2017 | Spiegelberg et al. | |
| 2018/0031414 A1* | 2/2018 | Farhadiroushan | G01V 1/226 |
| 2020/0348254 A1* | 11/2020 | Sheikh | G01N 33/0098 |
| 2021/0096106 A1* | 4/2021 | Ooi | G01N 29/2418 |
| 2022/0128384 A1* | 4/2022 | Hu | G01D 5/35361 |
| 2022/0225033 A1* | 7/2022 | Kojima | H04R 27/00 |
| 2022/0283022 A1* | 9/2022 | Ooi | G01D 5/35364 |
| 2022/0299481 A1* | 9/2022 | Ooi | G01N 29/14 |
| 2022/0408730 A1* | 12/2022 | Del Frari | A01N 63/30 |
| 2023/0160743 A1* | 5/2023 | Ashry | G01H 9/004 |
| | | | 73/655 |

FOREIGN PATENT DOCUMENTS

| | | | | |
|---|---|---|---|---|
| CN | 102401667 A | * | 4/2012 | |
| CN | 108225541 A | * | 6/2018 | |
| CN | 114674351 A | * | 6/2022 | ......... E21B 47/0002 |
| FR | 3122319 A1 | * | 11/2022 | |
| WO | WO-2018117946 A1 | * | 6/2018 | ........... G01N 29/041 |

OTHER PUBLICATIONS

Edirisinghe et al., WI-Alert a Wireless Sensor Network Based Intrusion Alert Prototype for Hec, International Journal of Distributed and Parallel Systems (IJDPS) vol. 4, No. 4, Jul. 2013, p. 14 (Year: 2013).*
Mankin et al., Acoustic Surveying of Subterranean Insect Populations in Citrus Groves, Ecology and Behavior, 2001, pp. 853-859 (Year: 2001).*
Potamitis al., Automatic Bioacoustic Detection of Rhynchophorus Ferrugineus, 16th European Signal Processing Conference (EUSIPCO 2008), Aug. 25-29, 2008, p. 4 (Year: 2008).*
Ashry et al., Early detection of red palm weevil using distributed optical sensor, Nature: Scientific Reports, 2020 (Year: 2020).*
Ashry et al., Towards Early Detection of Red Palm Weevil Using Optical Fiber Distributed Acoustic Sensor , Optical Fiber Communication Conference 2019 (OFC 2019) © OSA, San Diego, California United States, Mar. 3-7, 2019, p. 3 (Year: 2019).*
Estabrook, Thesis a Comparison of African Forest Elephant (*Loxondonta cyclotis*) Vocal Behavior and Gun Hunting Trends Between 2000 and 2018, Aug. 2022, p. 108 (Year: 2022).*
Dabare et al., Listening to the giants: Using elephant infra-sound to solve the human-elephant conflict, 2015, p. 4 (Year: 2015).*
Hussain et al., Intelligent System for White Grub Monitoring through WSN, International Journal of Current Advanced Research, 2017, p. 7 (Year: 2017).*
Mao et al., Monitoring the Red Palm Weevil Infestation Using Machine Learning and Optical Sensing, IEEE, 2021, p. 4 (Year: 2021).*
Rochester et al, Mountain Pine Beetle Monitoring with IoT, 2019 IEEE 5th World Forum on Internet of Things (WF-IoT), 2019, p. 6 (Year: 2019).*
Obrist et al., Flexible bat echolocation: the influence of individual, habitat and conspecifics on sonar signal design, Behav Ecol Sociobiol, 1995, 36:pp. 207-219 (Year: 1995).*
De la rosa et al, Subterranean Termite Detection Using the Spectral Kurtosis, IEEE International Workshop on Intelligent Data Acquisition and Advanced Computing Systems: Technology and Applications Sep. 6-8, 2007, Dortmund, Germany, p. 4 (Year: 2007).*
Mao et al., Towards Early Detection of Red Palm Weevil Using Optical Fiber Distributed Acoustic Sensor, IEEE, 2019, p. 3 (Year: 2019).*
Butterworth-Heinemann, Telecommunications Engineer's Reference Book Chapter 10, Elsevier Ltd., 1993, p. 14 (Year: 1993).*
Communication pursuant to Article 94(3) EPC in corresponding/related European Application No. 20721785.2, dated Oct. 24, 2023.
First Office Action in corresponding/related Chinese Application No. 202080045192.1, dated Sep. 23, 2023.
First Examination Report in corresponding/related Saudi Arabian Application No. 521430661, issued Mar. 14, 2023.
Gutierrez, A., et al., Development of a Bioacoustic Sensor for the Early Detection of Red Palm Weevil (*Rhynchophorus ferrugineus* Olivier), Crop Protection, Jul. 1, 2010, vol. 29, pp. 671-676, Elsevier Ltd.
Hetzroni, A., et al., "Toward Practical Acoustic Red Palm Weevil Detection," Computers and Electronics in Agriculture, Apr. 11, 2016, vol. 124, pp. 100-106, Elsevier B.V.
Hussein, W.B., et al., "Detection of the Red Palm Weevil *Rhynchophorus ferrugineus* Using its Bioacoustics Features," Bioacoustics. The International Journal of Animal Sound and its Recording, 2010, vol. 19, pp. 177-194, AB Academic Publishers.
International Search Report in corresponding/related International Application No. PCT/IB2020/053728, date of mailing Jul. 30, 2020.
Mankin, R.W., "Recent Developments in the Use of Acoustic Sensors and Signal Processing Tools to Target Early Infestations of Red Palm Weevil in Agricultural Environments1," Florida Entomologist, Dec. 2011, vol. 94, No. 4, pp. 761-765.
Mao, Y., et al., "Towards Early Detection of Red Palm Weevil Using Optical Fiber Distributed Acoustic Sensor," W2A. 15, Mar. 3, 2019, pp. 1-3.
Rach, M.M., et al., "On the Design of a Bioacoustic Sensor for the Early Detection of the Red Palm Weevil," Sensors, Jan. 30, 2013, vol. 13, No. 2, pp. 1706-1729.
Siriwardena, K.A.P., et al., Portable Acoustic Device for Detection of Coconut Palms Infested by *Rynchophorus ferrugineus* (Coleoptera: Curculionidae), Crop Protection, Sep. 4, 2009, vol. 29, pp. 25-29, Elsevier Ltd.
Written Opinion of the International Searching Authority in corresponding/related International Application No. PCT/IB2020/053728, date of mailing Jul. 30, 2020.
Lu, Y., et al., "Distributed Vibration Sensor Based on Coherent Detection of Phase-OTDR," Journal of Lightwave Technology, Nov. 15, 2010, vol. 28, No. 22, pp. 3243-3249, IEEE.
Liu, K., et al., "Multi-Area Optical Perimeter Security System with Quick Invasion Judgement Algorithm," Journal of Optoelectronics, Laser, Feb. 2015, vol. 26, No. 2, pp. 1-7.
Second Office Action in corresponding/related Chinese Application No. 202080045192.1, dated Jul. 9, 2024.
Communication pursuant to Article 94(3) EPC in corresponding/related European Application No. 20721785.2, dated Nov. 27, 2024.
Decision on Rejection in corresponding/related Chinese Application No. 202080045192.1, dated Nov. 30, 2024.

* cited by examiner

SIGNAL PROCESSING ALGORITHM FOR DETECTING RED PALM WEEVILS USING OPTICAL FIBER

CROSS-REFERENCE TO RELATED APPLICATIONS

This application is a U.S. National Stage Application of International Application No. PCT/IB2020/053728, which claims priority to U.S. Provisional Patent Application No. 62/836,882, filed on Apr. 22, 2019, entitled "SIGNAL PROCESSING ALGORITHM FOR DETECTING RED PALM WEEVILS USING OPTICAL FIBER," the disclosures of which are incorporated herein by reference in their entirety.

BACKGROUND

Technical Field

Embodiments of the subject matter disclosed herein generally relate to a system and method for detecting red palm weevils, and more particularly, to an algorithm that is configured to process data recorded with an optical fiber wrapped around a red palm to detect the presence of the red palm weevils.

Discussion of the Background

Red palm weevil (RPW) (*Rhynchophorus ferrugineus*) is a snout pest originating from tropical Asia. In the past few decades, it has spread out to many regions worldwide including North Africa, Middle East, and Mediterranean regions. This pest has wiped out many palm farms in different countries, so it is considered a very severe problem. In the Gulf countries and the Middle East, millions of dollars are spent yearly only to remove the infested palm trees. The cost to treat the infested palm trees could be even higher. Additionally, by 2023, it is estimated that RPW control cost and loss of benefits to be in the millions of dollars in Italy, Spain, and France.

The problem with this pest is that although there are available techniques to heal RPW infested palm trees, detecting the presence of the RPW threat at an early stage (first two/three weeks of the weevil larvae stage) is challenging. This is so because by the time a palm tree shows visible signs of distress, such as a sagging canopy, this generally means that the RPW infection is well-advanced and it is too late to rescue the tree. As a result, governments of many countries are committing to develop a reliable and efficient early detection approach to tackle this problem.

There are several methods that have been reported to tackle this sever danger. For instance, trained dogs are used to smell the gases released from infested palms during the fermentation processes. Unfortunately, sensing such kind of gases is not an accurate selective process because its efficiency is impacted by the presence of other volatile products. Alternatively, infested trees are screened with a computer-based tomography system. However, this technique lacks feasibility since it is slow and expensive.

The first detectable signals of an infested tree originate from the noise produced by the weevil larvae while eating within the trunk of the tree. Therefore, the most promising early detection methods rely on using acoustic sensors [1-5]. The existing technologies mainly insert a sound probe into the tree trunk such that the probe records larvae sound in real-time.

More specifically, the existing methods that use acoustic sensors, as illustrated in FIG. 1, primarily insert an acoustic probe 102, such as microphone, into a hole 104 drilled into a palm trunk 106 and then the probe records the sound produced by the beetles in real-time. The sound is recorded on a computer 108 that is connected to the acoustic probe 102. The differences among the methods that are using the acoustic sensor are mainly in the signal processing techniques implemented for processing the recorded sound. However, all these methods require in-situ monitoring.

For vast farms, checking palms one-by-one is labor-, time-, and cost-consuming. Moreover, a major drawback of these reported methods is that they do not offer continuous monitoring for palm trees. An alternative solution is where each palm is equipped with a corresponding sound probe, which is connected to a wireless communication interface so that data transfer can take place to a central server. This system may be powered via a solar panel. Although this method provides continuous observation for the individual palm trees, its overall cost is very high. Another disadvantage of the aforementioned acoustic methods is the damage done to the tree because of the hole made in the trunk for inserting the sound probe, the labor necessary to drill each tree, the impact of the hole on the growth of the palms, and the possibility of other insects to establish a nest into the holes made into the trunk.

Additionally, offering an acoustic sensor along with a wireless communication interface for each tree to provide continuous monitoring, significantly increases the cost of the entire RPW surveillance system given that a red palm tree orchard can have thousands of such trees.

Thus, there is a need for a new system and method that are capable of monitoring the sound generated by the RPW larvae, without generating interference and being high cost, and also for being able to distinguish the RPW larvae from other background noise. In addition, the new system is expected to not be invasive for the health of the tree.

BRIEF SUMMARY OF THE INVENTION

According to an embodiment, there is a method for determining tree infestation, and the method includes placing an optical fiber around a trunk of a tree, recording with a distributed acoustic sensor (DAS) box a Rayleigh signal reflected from the tree, along the optical fiber, processing the Rayleigh signal to obtain a processed signal, calculating a signal-to-noise ratio (SNR) of the processed signal for the tree, and comparing the SNR to a threshold value and counting an alarm if the SNR is larger than the threshold value. The SNR is defined as a ratio between (1) a maximum value of a processed signal and (2) a minimum value of the processed signal.

According to another embodiment, there is a system for determining tree infestation and the system includes an optical fiber that is configured to be placed around a trunk of a tree, a distributed acoustic sensor (DAS) box connected to the optical fiber and configured to record a Rayleigh signal reflected from the tree, along the optical fiber, and a processor. The processor is configured to process the Rayleigh signal to obtain a processed signal, calculate a signal-to-noise ratio (SNR) of the processed signal for the tree, and compare the SNR to a threshold value and count an alarm if the SNR is larger than the threshold value. The SNR is defined as a ratio between (1) a maximum value of a signal and (2) a minimum value of the processed signal.

According to yet another embodiment, there is a method for determining tree infestation in red palm trees, and the method includes recording with a distributed acoustic sensor (DAS) box a Rayleigh signal reflected from the red palm trees, wherein the Rayleigh signals is received from an optical fiber wounded around trunks of the red palm trees; processing the Rayleigh signal to obtain a processed signal; calculating a signal-to-noise ratio (SNR) of the processed signal for a given tree; and comparing the SNR to a threshold value and counting an alarm if the SNR is larger than the threshold value. The SNR is defined as a ratio between (1) a maximum value of a signal and (2) a minimum value of the processed signal.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Figure 1:
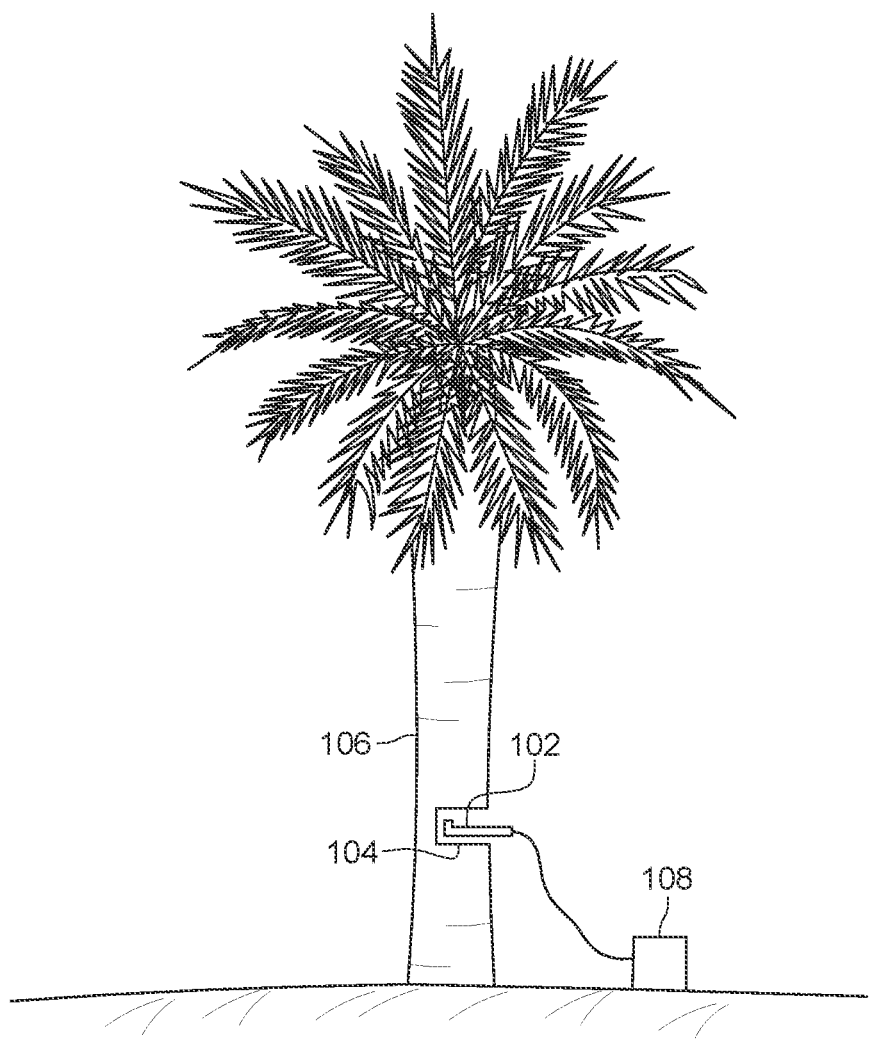
FIG. 1 is a schematic diagram of a red palm tree having its trunk drilled to place an acoustic sensor.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to an distributed acoustic sensor (DAS) system that is used to determine the presence of a RPW larvae. However, the embodiments to be discussed next are not limited to determining the presence of the RPW larvae in a red palm, but may be applied to any tree infestation caused by a bug, or to other applications in which a fine noise needs to be detected and classified.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, an optical fiber distributed acoustic sensor (DAS) is introduced as a robust solution for the early detection of RPW. In one implementation, all of the optical/electronic components, such as a laser, photodetector, amplifier, circulator, etc., are gathered within a single unit and one or more optical fibers are connected to this unit. The one or more optical fibers is wound around one or more of the palm trees, thus forming an optical network. As discussed next, this system is used to distinguish two palm trees, one which is healthy and another one that is infested with an about 12 days old larvae. In comparison to the existing acoustic sensors systems discussed in the Background section, the DAS system is unique by providing noninvasive monitoring, continuous surveillance with relatively low cost, and spacious farm area coverage with using a single optical fiber cable. Of course, it is possible to use plural optical fibers with this system.

Prior to discussing the details of the new method, the DAS system is introduced. The underlying operation concept of an optical fiber DAS relies on using a coherent (narrow linewidth) laser source to launch optical pulses into a fiber. While a pulse is propagating along the fiber, a Rayleigh trace is backscattered from the fiber and it is recorded at the fiber input port. By monitoring the intensity's temporal evolution of the recorded Rayleigh traces, it is possible to accurately calculate a position along the fiber, which was subjected to an acoustic signal and to determine its frequency. If the frequency belongs to the range of frequencies emitted by the RPW, then it is determined that the RPW is present in the tree.

Figure 2:
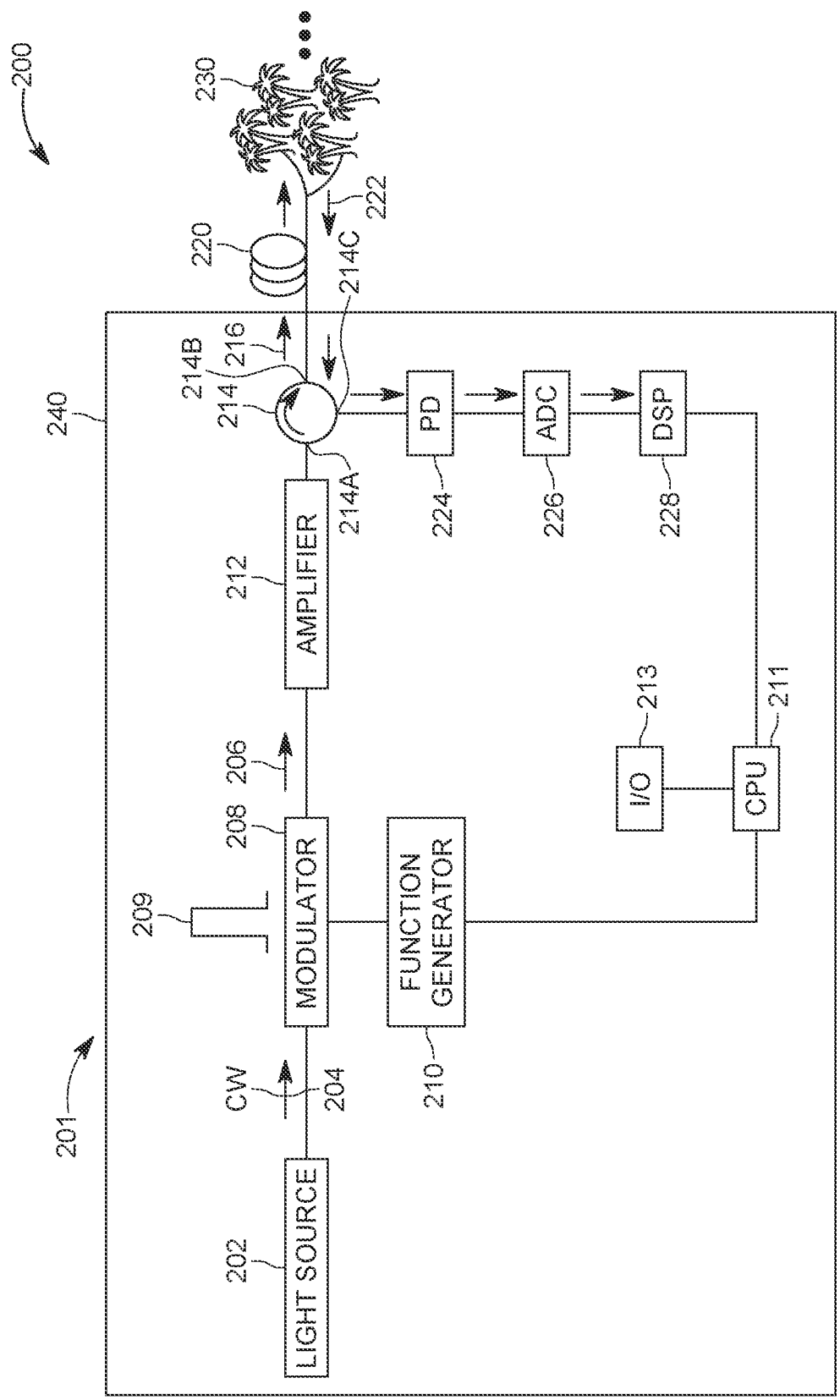
FIG. 2 illustrates a distributed acoustic sensor system that is used to monitor a tree.

In this regard, FIG. 2 shows a fiber optic DAS system 200 that is capable of measuring a strain exerted on the optical fiber by changes in pressure, temperature and/or acoustic noise. System 200 has two main components, a DAS box 201 and the optical fiber 220, which is connected to the DAS box 201. The DAS box 201 includes all the electronics for generating a light beam, sending the light beam into the optical fiber, receiving a reflected light from the optical fiber, and processing the reflected light for detecting the RPW. More specifically, the DAS box 201 includes a light source 202 that is configured to generate continuous-wave (CVV) light 204 that is coherent. For example, the light source 202 may be a laser or a light-emitting diode. The CW light 204 is converted to optical pulses 206 via a light modulator 208. The light modulator 208 is connected to a function generator 210. The function generator 210, which can be controlled by a computing device 211, is configured to generate a mathematical function to be applied to the modulator to modulate the light 204. For example, FIG. 2 shows the modulator 208 applying a rectangular pulse 209 to the light 204, to obtain the optical pulses 206 (or modulated light). Other shapes may be used for the pulse 209. The computing device 211 is also connected to an input/output module 213, which is capable of communicating, for example, in a wireless or wired manner with a smartphone, personal computer, or any other electronic device for both sending messages and also for receiving instructions.

Optionally, the system 200 includes an amplifier 212 for amplifying the modulated light 206, prior to launching it through a circulator 214 into the optical fiber 220. FIG. 2 schematically shows the optical fiber 220 being directed to plural trees 230. The circulator 214 may be, for example, a three- or four-port optical device designed such that light entering any port exits from the next port. This means that if light enters a first port 214A, it is emitted from a second port 214B. However, if some of the emitted light 216 is reflected back to the circulator 214, it does not come out of the first port 214A, but instead exits from a third port 214C. This makes possible that a reflected Rayleigh signal 222, after reaching the circulator 214, is directed toward a photodetector 224, instead of being sent toward the amplifier 212.

While the optical pulse 216 is propagating along the fiber 220, the Rayleigh signal 222 is backscattered from the trees 230. In the backward direction, the Rayleigh signal is recorded via the photodetector 224 and then sampled using an analog-to-digital converter (ADC) 226. A digital signal processing (DSP) 228 may be used to filter out the RPW sounds in the frequency domain and exactly identifies the locations of the infected palm trees 230 using, for example, the time domain signal. The optical fiber 220 may be a single-mode fiber (SMF). At the fiber input port, consecutive Rayleigh backscattered traces are recorded in the time domain. Each Rayleigh trace has a speckle-like profile because of coherent interference of the signals reflected by scattering centers within the injected pulse duration. In the absence of intrusions along the optical fiber, i.e., no refractive index perturbation, the recorded Rayleigh traces are ideally identical. In the case that an acoustic signal is applied at a position along the fiber, such as the weevil larvae sound, the effective refractive index changes at this position and consequently, the intrusion could be sensed by observing the intensity fluctuations of its corresponding speckle in the recorded traces.

By monitoring the intensity temporal evolution of the recorded Rayleigh signals 222, one can accurately figure out a position along the optical fiber 220 which was subjected to an acoustic signal emitted by the RPW and thus, determine the location of the RPW. For the purpose of RPW early detection, the system 200 shown in FIG. 2 outweighs the existing acoustic sensors in the literature because of at least one of the following reasons: 1) it would provide non-stop monitoring for palm trees with a relatively low price, 2) the sensing length of the typical optical fiber DAS is around 10 km, which could cover spacious farm area, 3) by using an optical switch and time-division-multiplexing (TDM), several fibers can be attached to the same DAS box, in case that monitoring larger farm areas is demanded, 4) no invasive sensing is required since the optical fiber would be wounded externally around the palms, and 5) the optical fiber used for acoustic sensing can simultaneously monitor ambient temperatures, with a resolution less than 0.1° C., which is considerably important to control farm fires, which is another major problem around the world.

In one embodiment, all the elements of the system 200, except the optical fiber 220, may be placed in a single housing 240, called herein the DAS box 201. This means that all of the optical components such as laser, photodetector, etc., are gathered within the DAS box, for example, at a control master station, whereas only the optical fiber 220 is wounded around the palm trees 230 in a form of optical network.

Figure 3A:
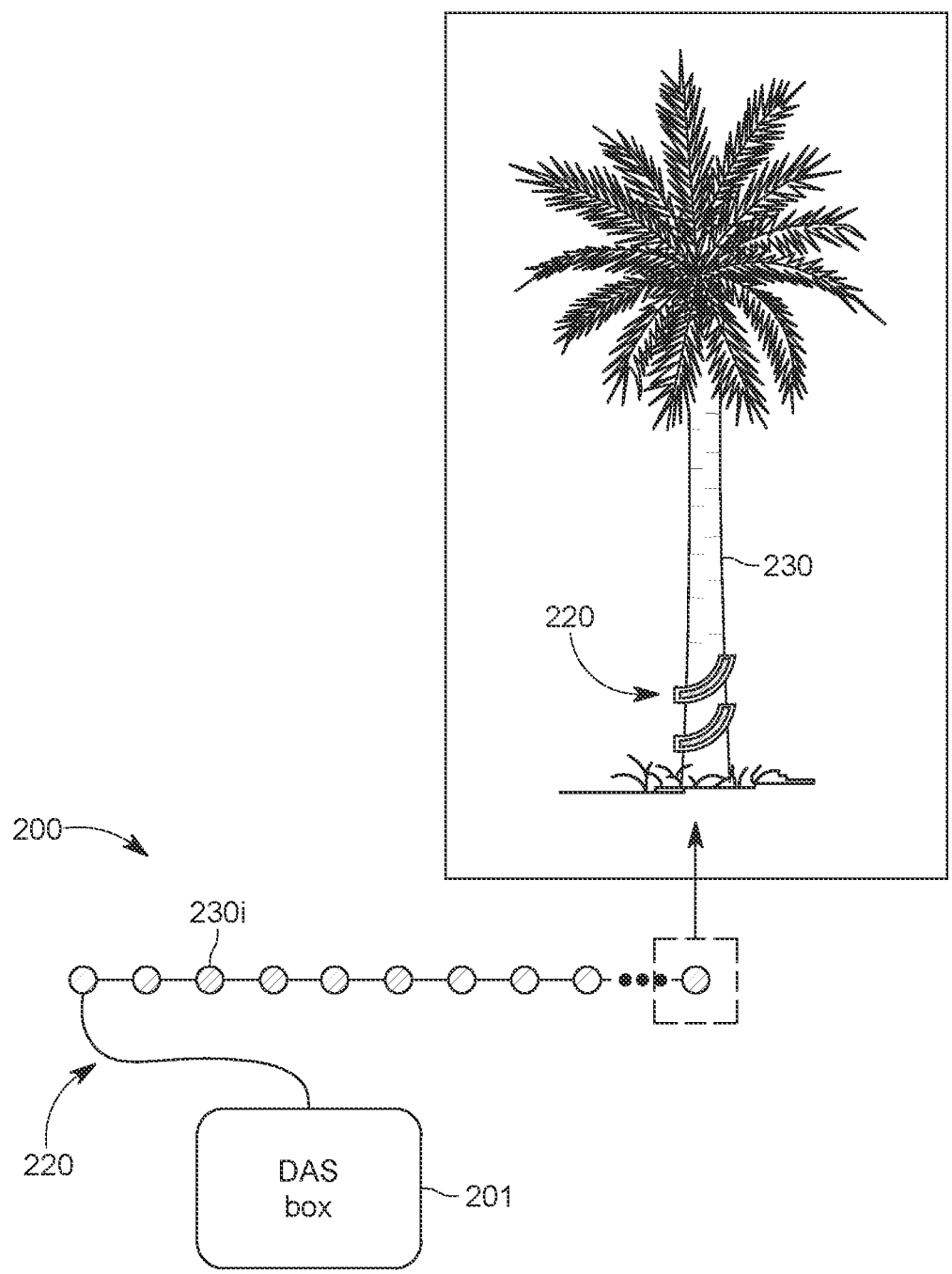
FIGS. 3A to 3E illustrate various implementations of the distributed acoustic sensor system.

The optical fiber 220 can be distributed along one or more trees. For example, FIG. 3A shows an embodiment in which the DAS box 201 is connected to a single optical fiber 220, which extends at plural trees 230$i$, where i is any natural number. The same optical fiber 220 can be rolled around each tree 230$i$, for example, from the ground up to about 1 m height on the trunk of the tree, where the probability of finding the RPW larva is the highest. However, other heights may be used. Between the trees, the optical fiber cable can be either laid down on the ground or buried in the soil, based on the environmental conditions. In another embodiment illustrated in FIG. 3B, a single DAS box 201 and a single optical fiber 220 are used to monitor plural trees 230$i$. However, in this embodiment, the trees are not just a line of trees as in the embodiment of FIG. 3A, but plural lines 232$j$ of trees, with j being a natural number. Note that in this embodiment, the same optical fiber 220 extends along each line 232$j$ of trees 230$i$.

Figure 3B:
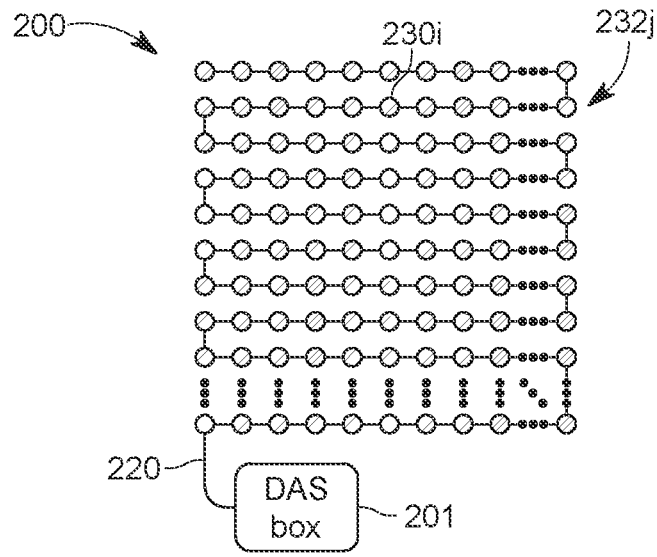
Figure 3C:
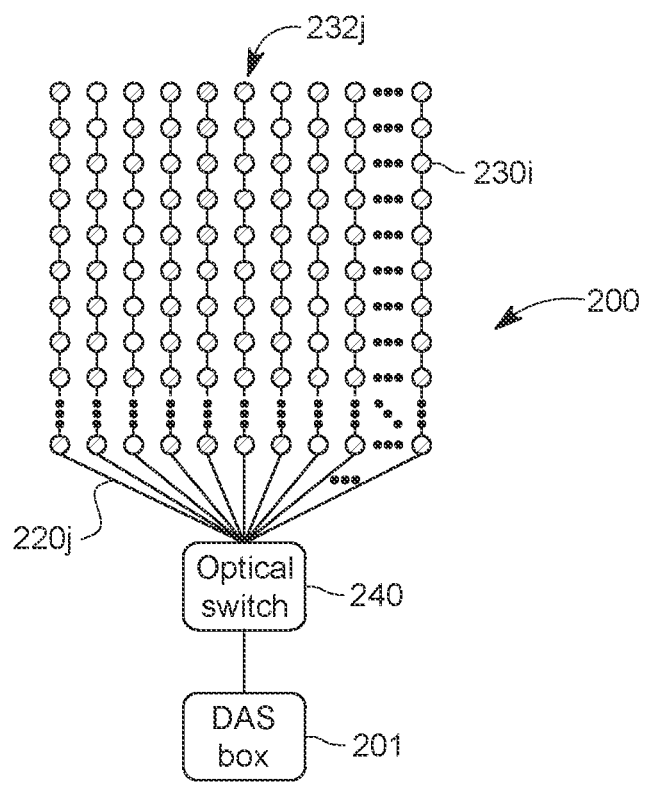

In yet another embodiment illustrated in FIG. 3C, plural optical fibers 220$j$ are distributed from a single DAS box 201, to plural lines 232$j$ of trees 230$i$. An optical switch 240 may be used to connect each optical fiber 220$j$ to a corresponding line 232$j$ of trees 230$i$. The optical switch 240 may be programmed to connect each optical fiber 220$j$, for a given time, to the DAS box 201, enough to get information to determine whether RPW are present in the trees or not. In this regard, note that there is no need to monitor the entire day a line of trees or a single tree for determining that RPW are present. Intermittent monitoring of the trees, for example, every hour or every couple of hours or even every day or every couple of days could be enough for determining the RPW presence. In one application, time multiplexing may be implemented over the optical switch 240 for optical switching.

Thus, the topology of the optical fiber DAS network, as illustrated in FIGS. 3A to 3C is quite flexible and can be adapted to fit almost any spatial distribution of palm trees in a small or large farm. If the sum of the separations between consecutive trees, including the lengths of the optical fibers wounded around trees, is within the sensing range of the DAS system 200, one optical fiber is sufficient to cover the whole farm, as illustrated in FIGS. 3A and 3B. Otherwise, for extremely large farms, multiple optical fibers 220$j$ can be connected through an optical switch to the DAS box, as illustrated in FIG. 3C. Because the sensing speed is not a considerable factor in this application, rotating the optical switch 240 around the different fibers 230$j$ would provide continuous monitoring to the whole farm.

Figure 3D:
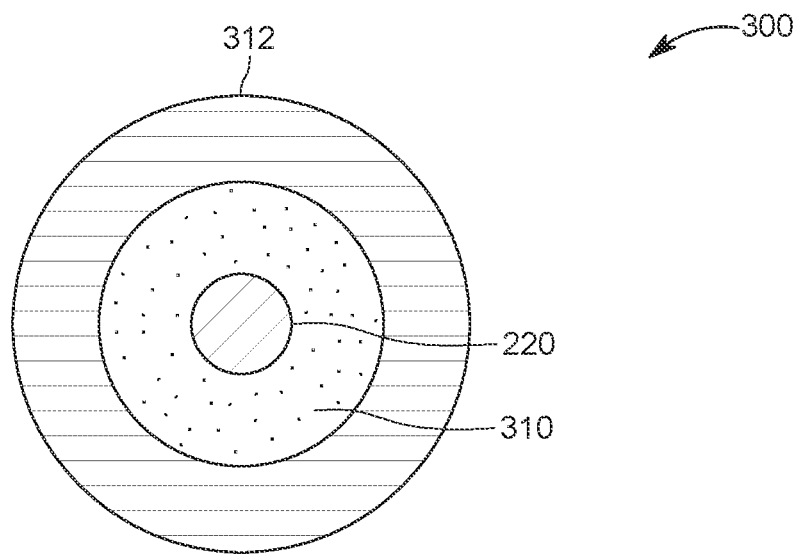
Figure 3E:
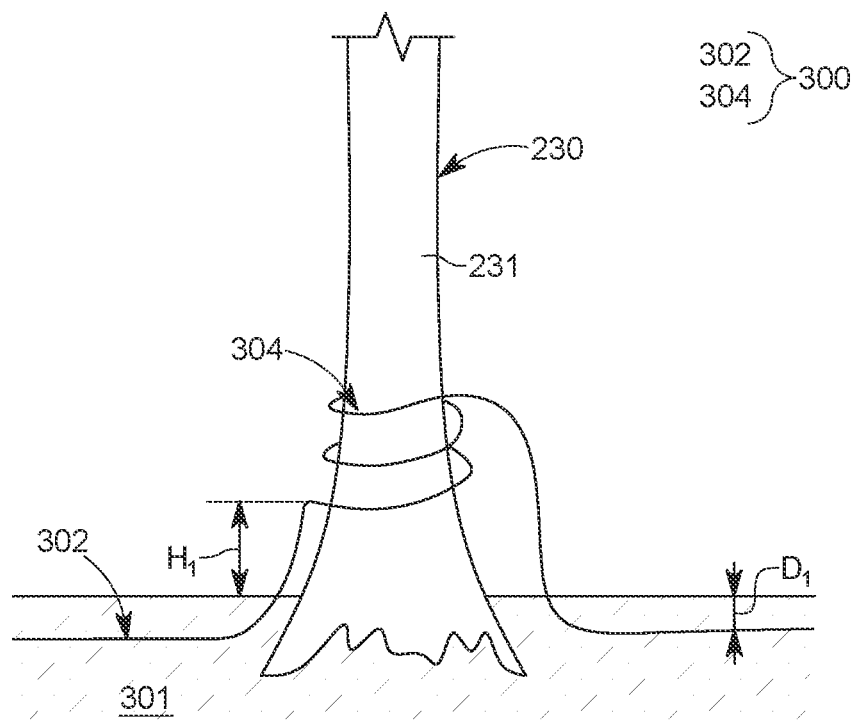

The optical fiber 220 may be wounded around the trunk of the tree 230 by itself, as shown in FIG. 3A, or protected by a cover layer as illustrated in FIGS. 3D and 3E. More specifically, FIG. 3D shows the optical fiber 220 being completely surrounded by a filler material 310, for example, cotton or similar fiber material, and an exterior shield layer 312. This optical fiber assembly 300 may have the exterior shield layer 312 made to fully enclose the filler material and the optical fiber. The exterior shield layer 312 may be made from a rigid material (e.g., steel tube or pipe, plastic pipe) or from a flexible material (e.g., flexible metallic or plastic pipe, etc.). In one embodiment, the exterior shield layer 312 is rigid for a portion of the optical fiber and flexible for another portion of the optical fiber.

For example, as illustrated in FIG. 3E, the optical fiber assembly 300 has a first portion 302 that is fully buried in the ground 301, and a second portion 304 that is wounded around the trunk 231 of the tree 230. The first portion 302 may be made to be rigid while the second part 304 may be made to be flexible, to allow it to wound around the trunk of the tree. The purpose of the filler material and the exterior shield layer 312 is to protect the optical fiber 220 from mechanical or thermal damage while being deployed in the field. In this regard, note that in a farm there is heavy equipment that move around the trees for various agricultural procedures. In one application, the depth D1 at which the first portion 302 is buried into the ground is between 0.5 to 2 m. A height H1 at which the optical fiber assembly starts to wound around the trunk 231 is about 0.5 to 3 m for best efficiency, as the weevil larva tends to attack the trunk at these heights. A length of the optical fiber 220 that is present in the second portion 304 is between 1 and 10 m. Other numbers for the parameters discussed herein may be used.

Figure 4:
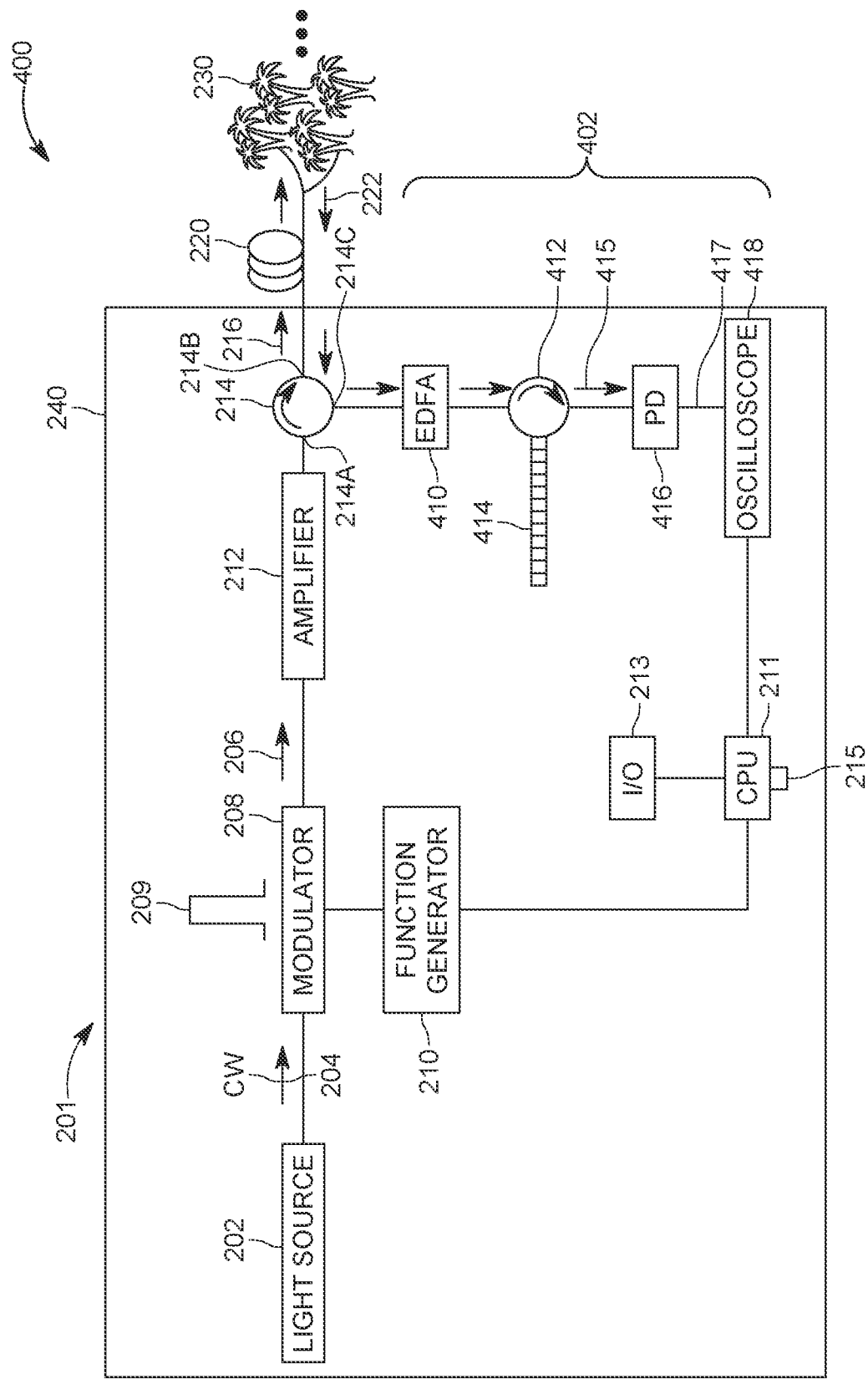
FIG. 4 shows a modified distributed acoustic sensor system that has a filter capability.

For the detection method to be discussed next, the system 400 illustrated in FIG. 4 is used. The system 400 is similar to the system 200 of FIG. 2, except for the detection part. The system 400 has the laser source 202 generating a CW light 204 of 100 Hz linewidth, 16 dBm optical power, and 1535 nm operation wavelength. The laser light is modulated by the acousto-optic modulator (AOM) 208, which is driven by the pulse generator 210 to produce optical pulses 206 of 20 kHz repetition rate and 100 ns width, which offers 10 m sensing spatial resolution. Next, the power of the modulated light is amplified using an erbium-doped-fiber-amplifier (EDFA) 212 and then injected through the circulator 214 into the SMF 220, which is about 1.1 km long in this embodiment. The optical fiber may have any length between 100 m and 20 km. The backscattered Rayleigh signal 222 from the SMF 220 is recorded using a direct detection scheme 402, as shown in FIG. 4. The Rayleigh signal 222 is initially amplified with another EDFA 410, whose amplified spontaneous emission noise is discarded by a fiber Bragg grating (FBG) 414. The filtered Rayleigh signal 415 passes through a second circulator 412 and is recorded via a photodetector (PD) 416. Then, the recorded signal 417 is sampled at 125 MS/s rate using an oscilloscope 418, and processed, for example, at processor 211, to extract the sensing information, which is discussed later. The processor 211 may apply a filter 215, which is implemented in software or hardware or both, to eliminate certain noise that is associated with an environment in which the tree is present.

Figure 5:
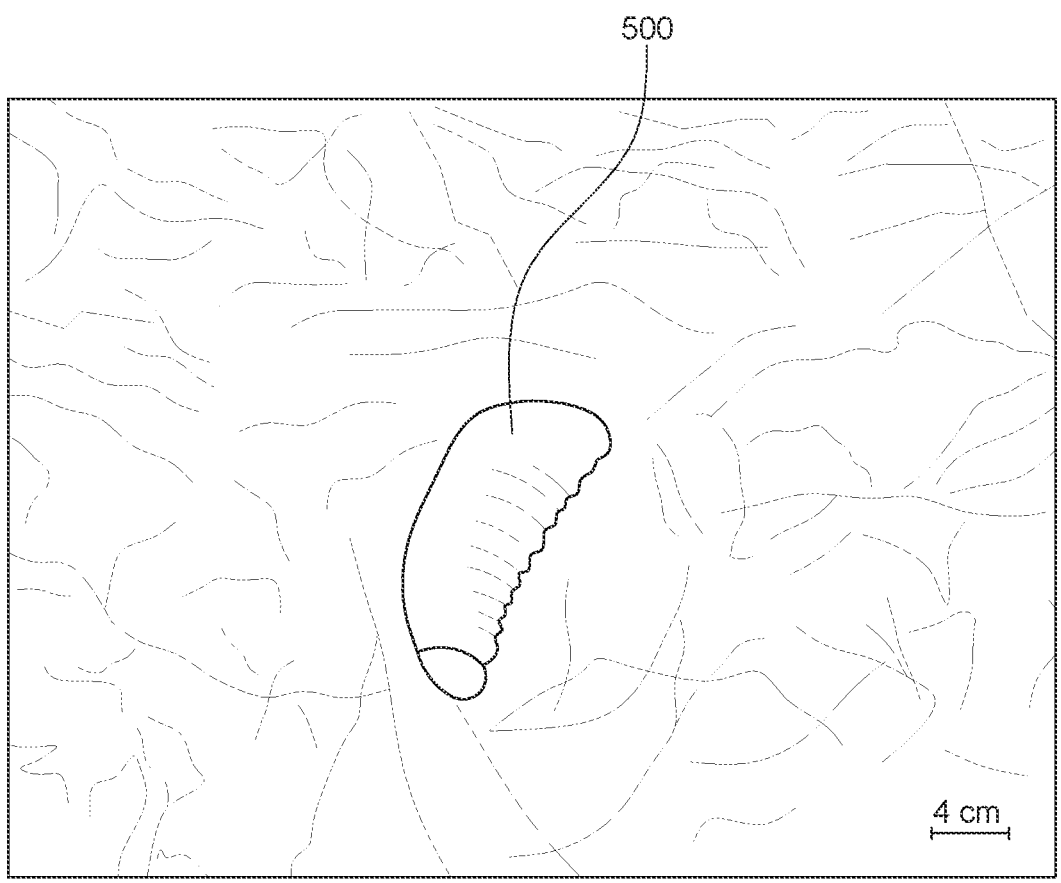
FIG. 5 illustrates the larva of a red palm weevil.
Figure 6A:
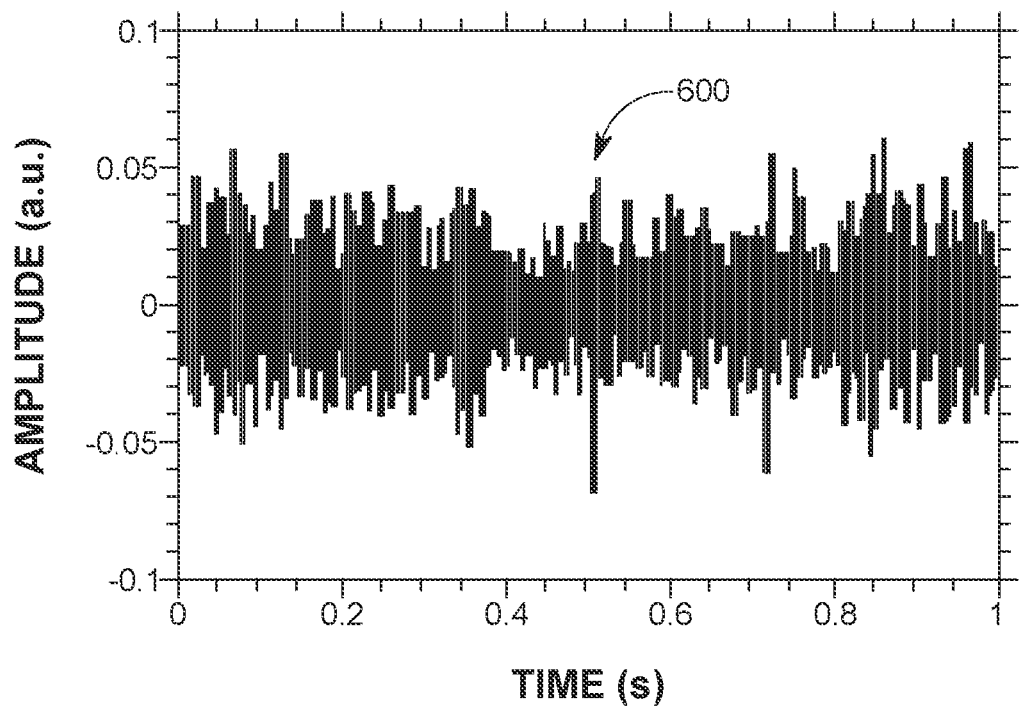
FIGS. 6A to 6D illustrate the sound signature of the larva when recorded with a microphone deployed in the trunk of a tree.
Figure 6B:
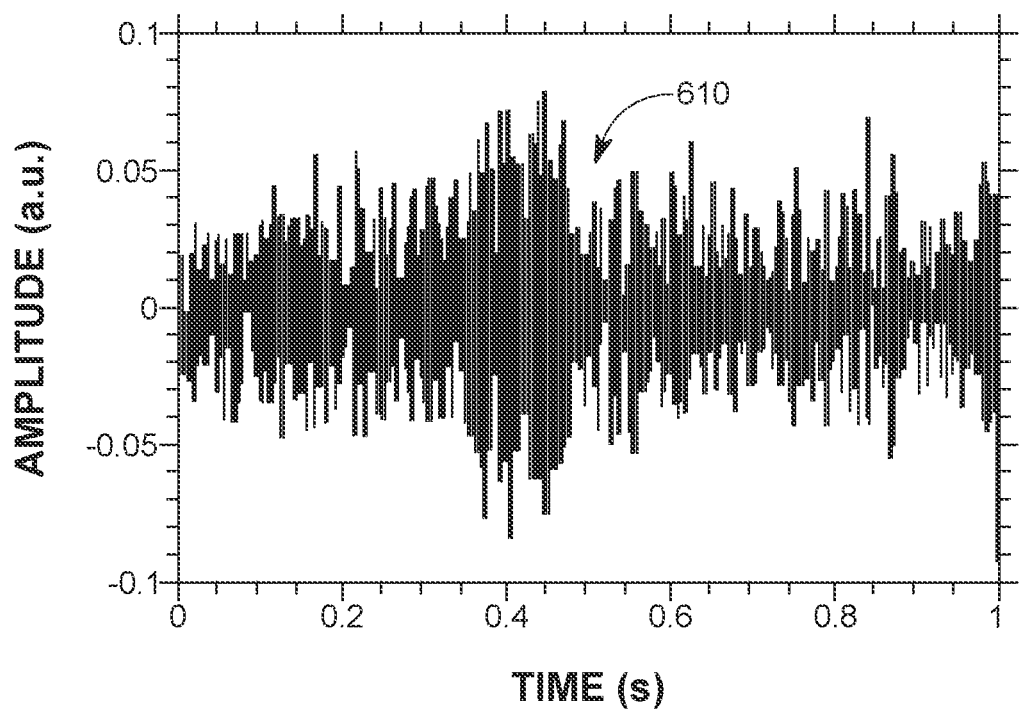
Figure 6C:
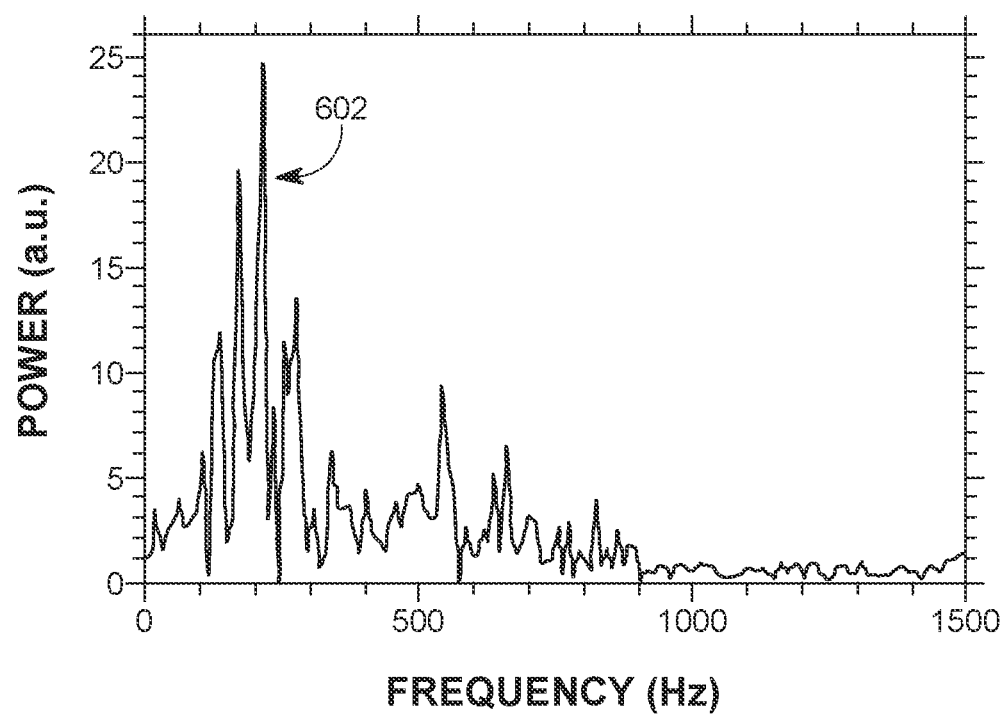
Figure 6D:
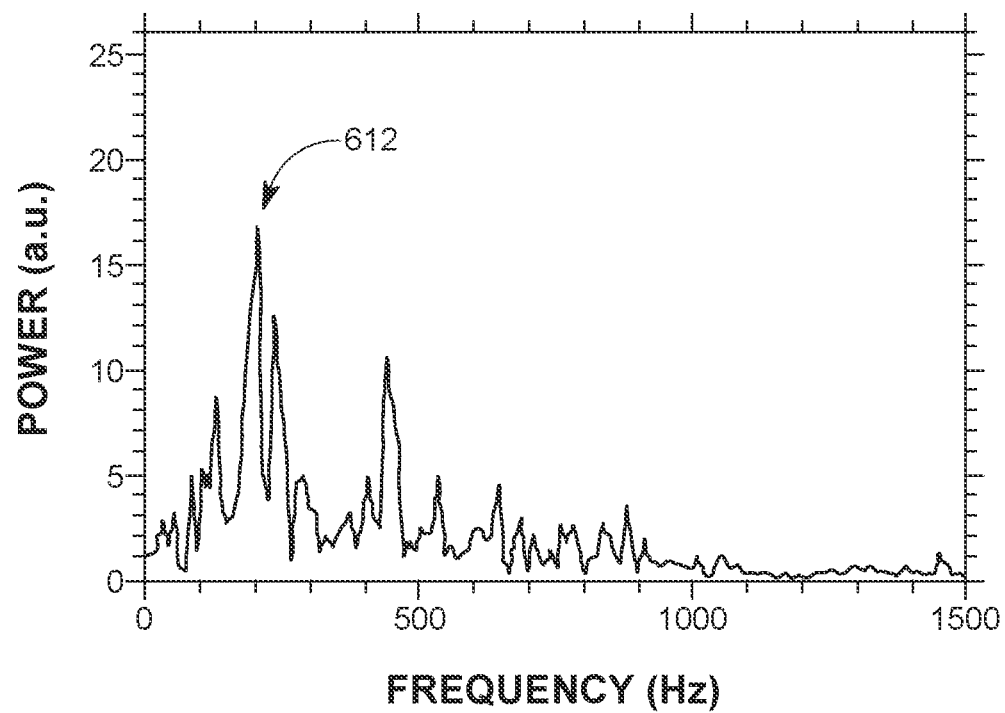

Using the system 400 illustrated in FIG. 4, the sound spectrum signature of the weevil larvae of an age less than two weeks was measured. For this embodiment, this specific RPW life stage was selected because the inventors have found that if the system 400 can detect the larvae sound at this early stage, the infested palm tree could be cured. To get control on the weevil larvae age, a palm tree was artificially infested with male and female beetles and the transition from the egg- to larvae-stage was monitored. In particular, the inventors performed measurements using an artificially infested sample tree that includes 4-6 pieces of ~12 days old larvae 500, which are illustrated in FIG. 5. Recognizing the sound spectrum signature of the larvae 500 will facilitate the signal processing algorithm that was developed to locate infested trees using the optical fiber DAS system 400, as will be discussed in details later. To measure this sound spectrum signature, a commercially available voice recording microphone was used. These measurements are performed by inserting the microphone within the trunk of the artificially infested palm tree (similar to the configuration shown in FIG. 1) to be in close proximity to the larvae. Two representative examples of the time domain larvae sound 600 and 610, which were recorded via the microphone, are shown in FIGS. 6A and 6B. FIGS. 6A and 6B plot the amplitude (arbitrary units) of the recorded sound versus time (measured in seconds) and FIGS. 6C and 6D illustrate their corresponding power spectra 602 and 612, respectively. FIGS. 6C and 6D show the power, in arbitrary units, represented as a function of the frequency.

Figure 7A:
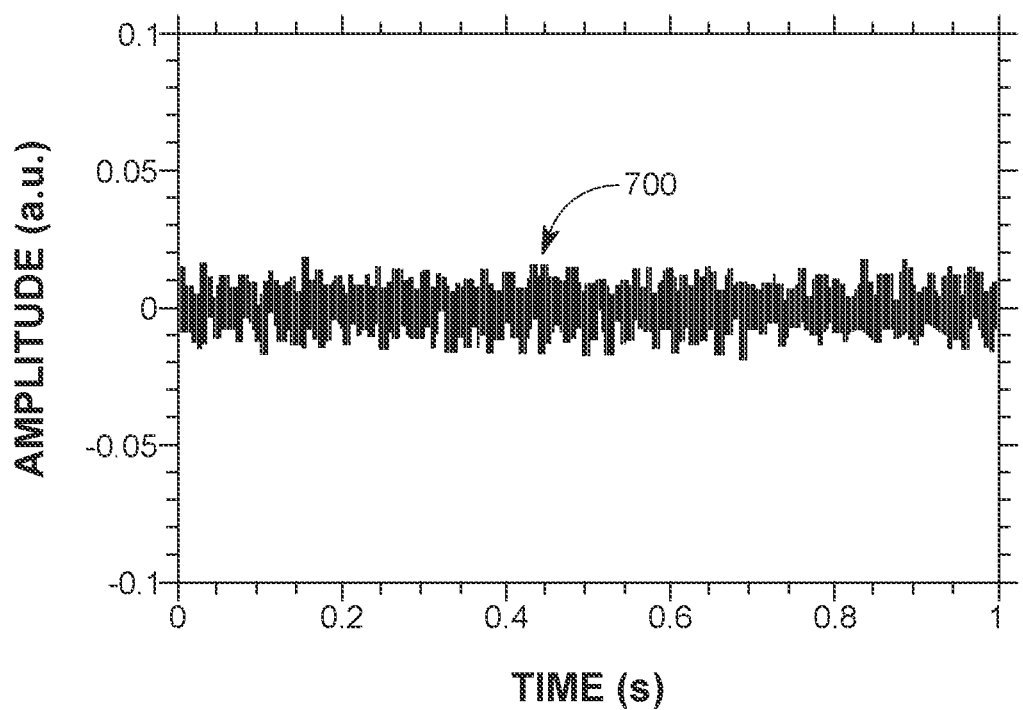
FIGS. 7A and 7B illustrate the ambient noise for the trunk of the tree.
Figure 7B:
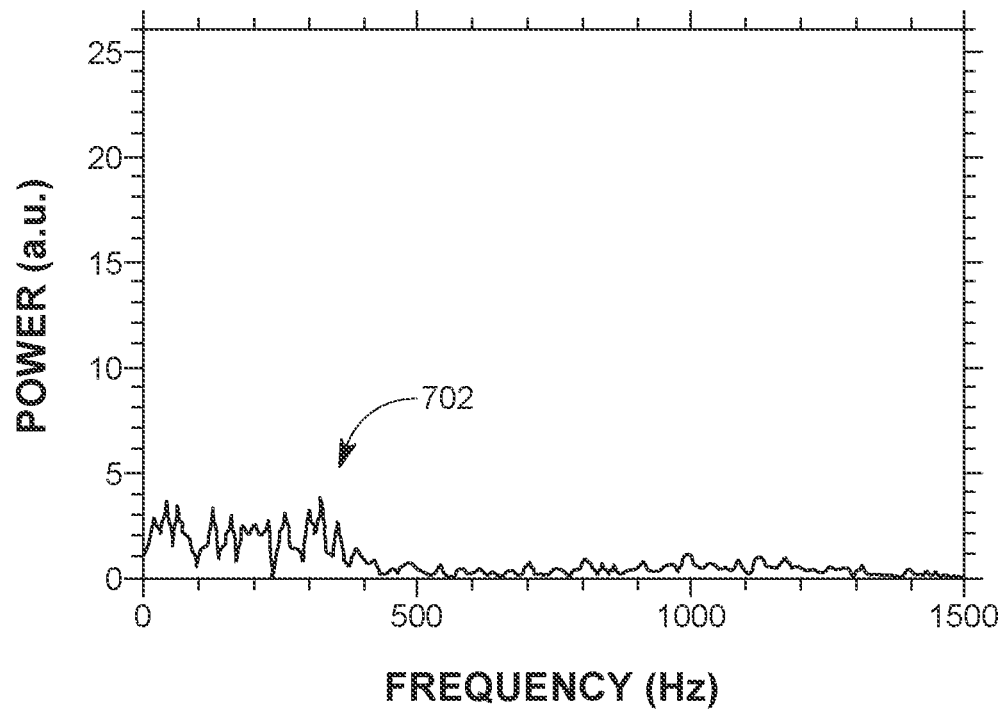

It can be observed from the power spectra in FIGS. 6C and 6D that the larvae sound is mostly emitted at frequencies within the range below ~800 Hz, which might also include some environmental noise signals. In this regard, FIGS. 7A and 7B show an example for the time domain signal spectra 700 and power spectra 710 of the background noise recorded via the microphone without the presence of the larvae. It is worth mentioning that both of the larvae sound and noise are recorded exactly under the same setting parameters for the microphone. Therefore, their signal strengths in the time and frequency domains in FIGS. 6A to 7B can be compared with each other. In contrast to the larvae sound 600 and 610, the noise signal 700 is weaker and with almost flat fluctuations in the time domain, and its power 702 is roughly equally distributed among the low frequencies, i.e., below ~400 Hz, as illustrated in FIG. 7B. The power spectra results of the larvae sound 602 and 612 and the background noise 702 are in good agreement with experiments of the inventors' previous work [6].

Figure 8A:
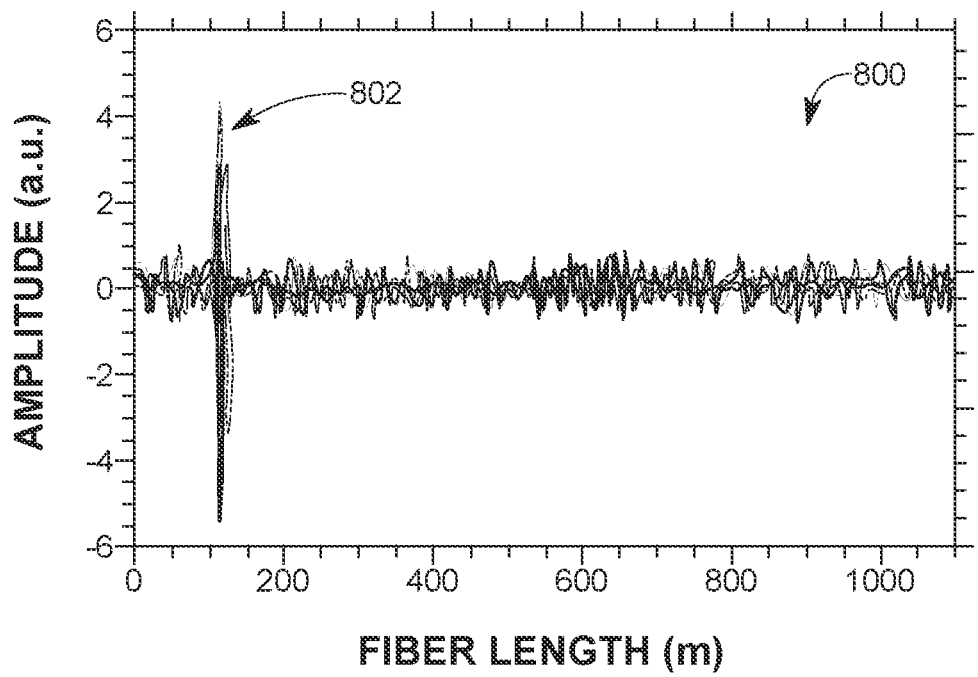
FIGS. 8A and 8B illustrate the calibration of an optical fiber with a manmade source.
Figure 8B:
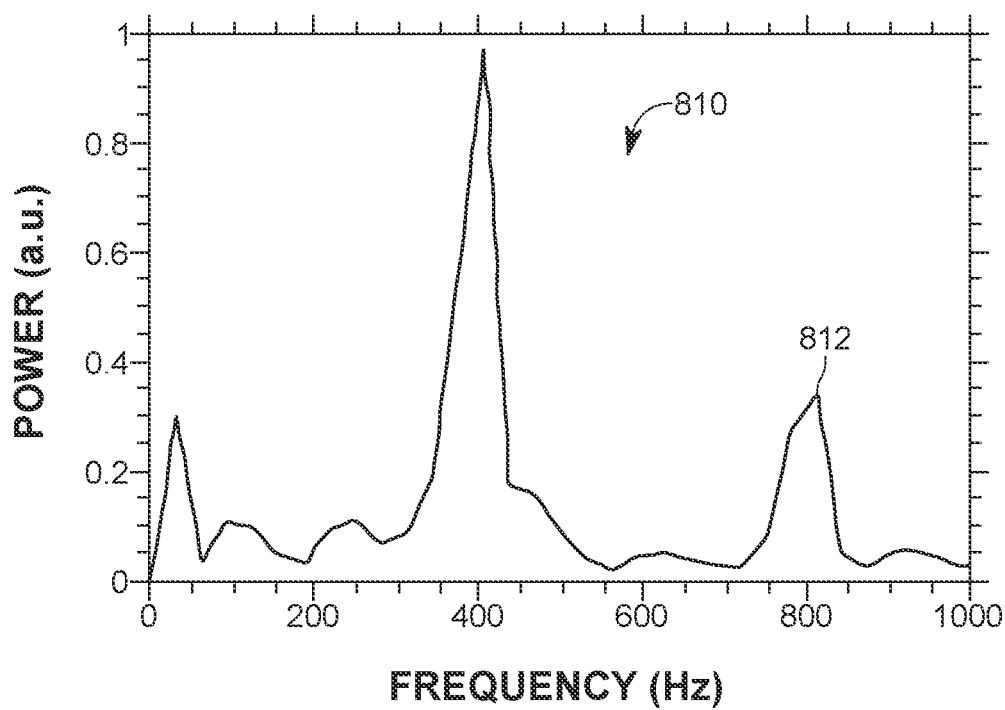

Before using the DAS system 400, shown in FIG. 4, to record the weevil larvae sound, the system was calibrated to make sure the used DAS box 201 can accurately figure out a location along the SMF 220 subjected to acoustic signals and also it can determine the frequencies of these signals. For such calibration purpose, at a distance of about ~110 m from the SMF 220 input facet, a 10 m portion of the optical fiber 220 was wounded around a piezoelectric transducer (PZT) cylinder (not shown). The PZT cylinder acts as a vibration source that has a known response (signature). The PZT cylinder is conventionally used for optical fiber DAS calibration because its vibration amplitude and frequency can be predetermined using a driven function generator. As described in [7], the vibration location along the optical fiber 220 can be obtained by subtracting the subsequent Rayleigh traces in the time domain. After identifying the vibration location, a Fourier transform may be applied to the Rayleigh traces at this location to determine the signal frequency components. In this regard, FIG. 8A shows the location information 800 generated with the PZT cylinder. FIG. 8A plots the amplitude, in arbitrary units, of the recorded signal versus the length of the optical fiber, with the location 802 of the PZT source clearly visible, while FIG. 8B shows the power spectrum 810 of a 400 Hz PZT vibration event. These results confirm the ability of the optical fiber DAS system 400 to identify the vibration location along with its frequencies. The high-order harmonics 812 appeared at 800 Hz in FIG. 8B is because of the nonlinearity of the direct detection scheme.

Next, the measurements previously discussed with regard to FIGS. 6A to 7B were repeated, and this time both the larvae sound and the background noise were recorded using the optical fiber DAS system 400, instead of the voice recording microphone. Near the SMF 220's end, a 10 m fiber section was placed around the same infested tree used during the former voice recording microphone experiment. Based on the results obtained when using the microphone, a band-pass filter of [200 Hz, 800 Hz] range was applied on the time domain signals collected by the optical fiber DAS system 400. This filter should discard most of the low-frequency environmental noise, such as tree swinging [6], and the high-frequency electronic noise introduced by the system 400. The band-pass filter 215 allows the system to collect the majority of the larvae sound signal.

Figure 9A:
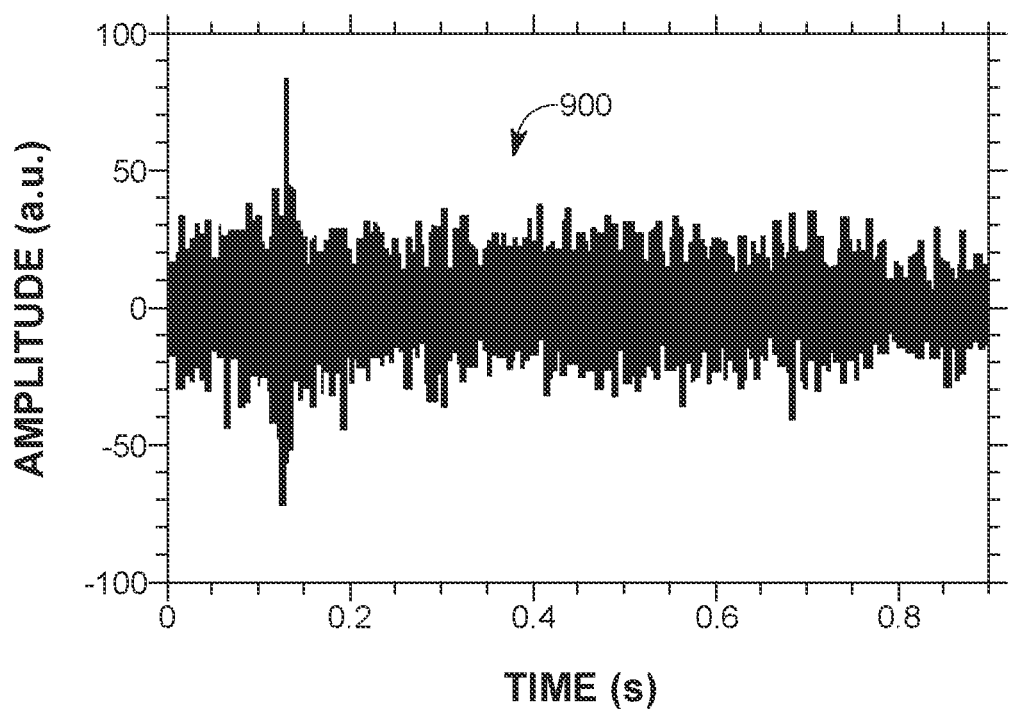
FIGS. 9A to 9D illustrate the filtered sound signature of the larva when recorded with the DAS system having the optical fiber wounded around the trunk of the tree.
Figure 9B:
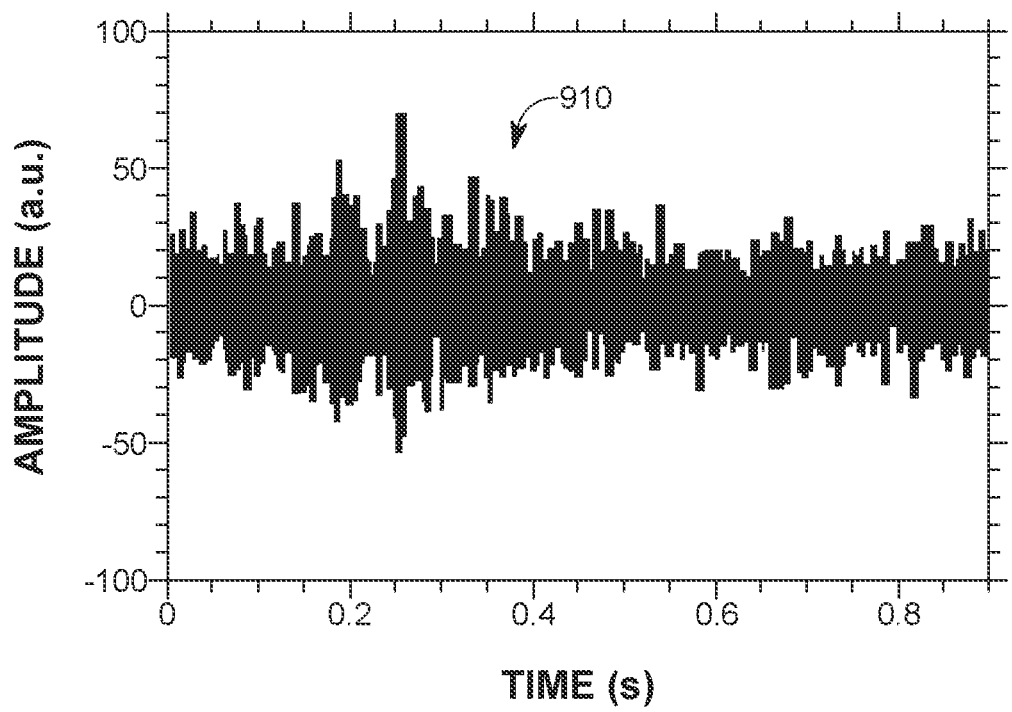
Figure 9C:
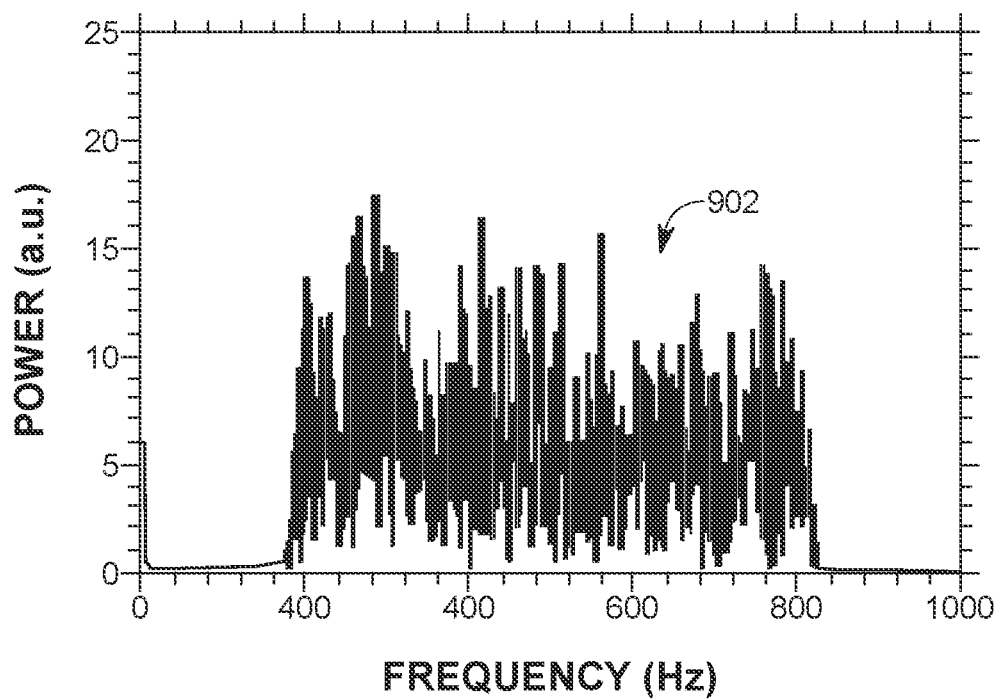
Figure 9D:
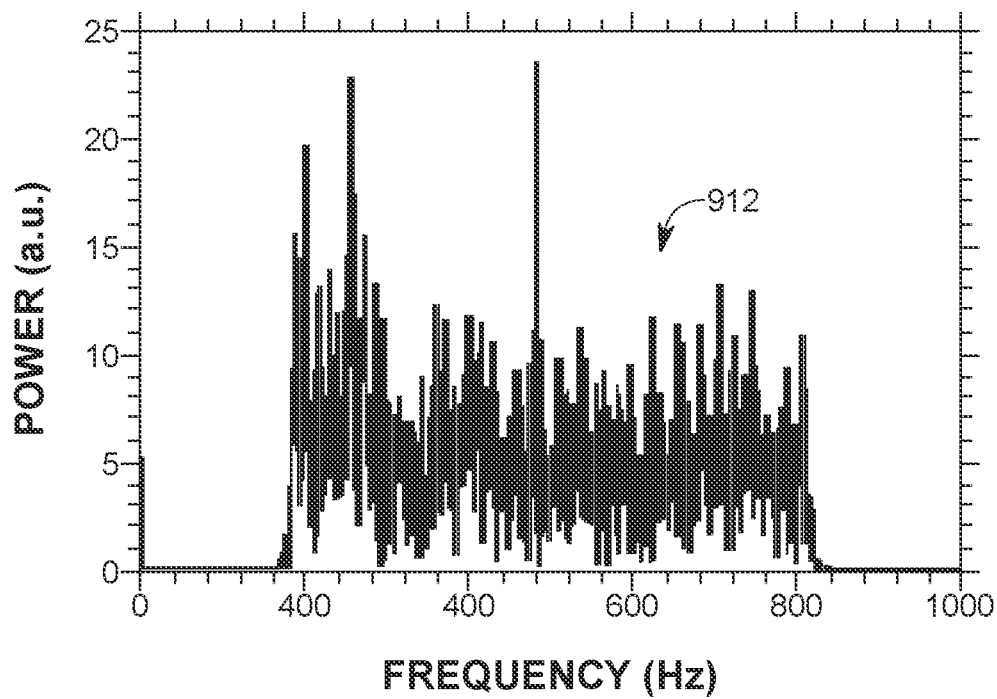
Figure 10A:
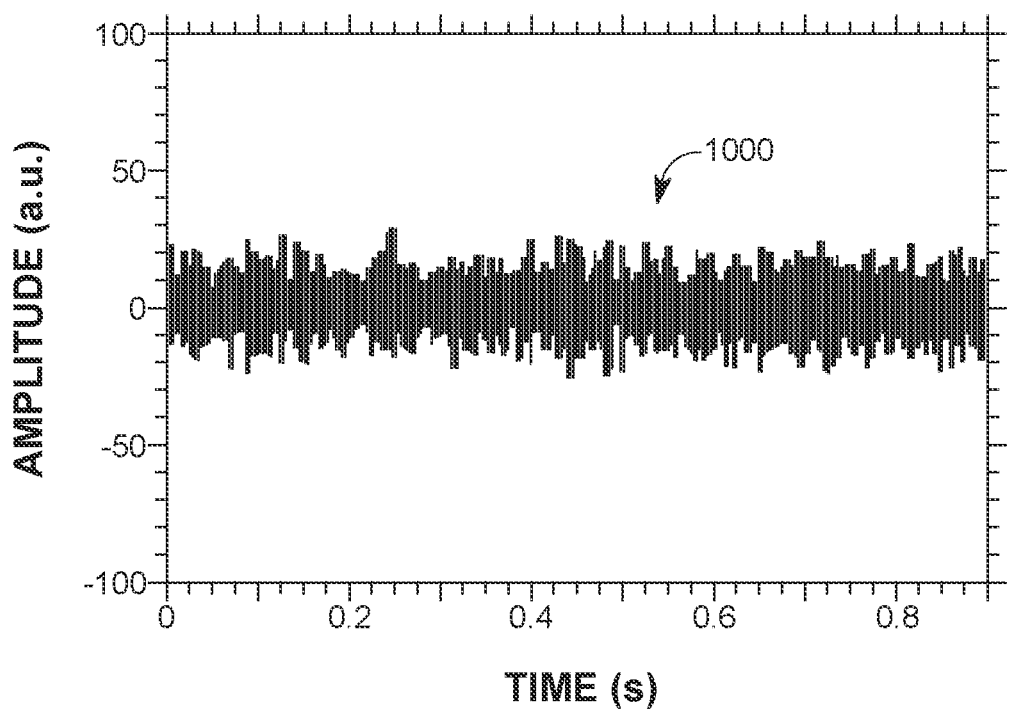
FIGS. 10A and 10B illustrate the sound signature of the noise associated with the tree.
Figure 10B:
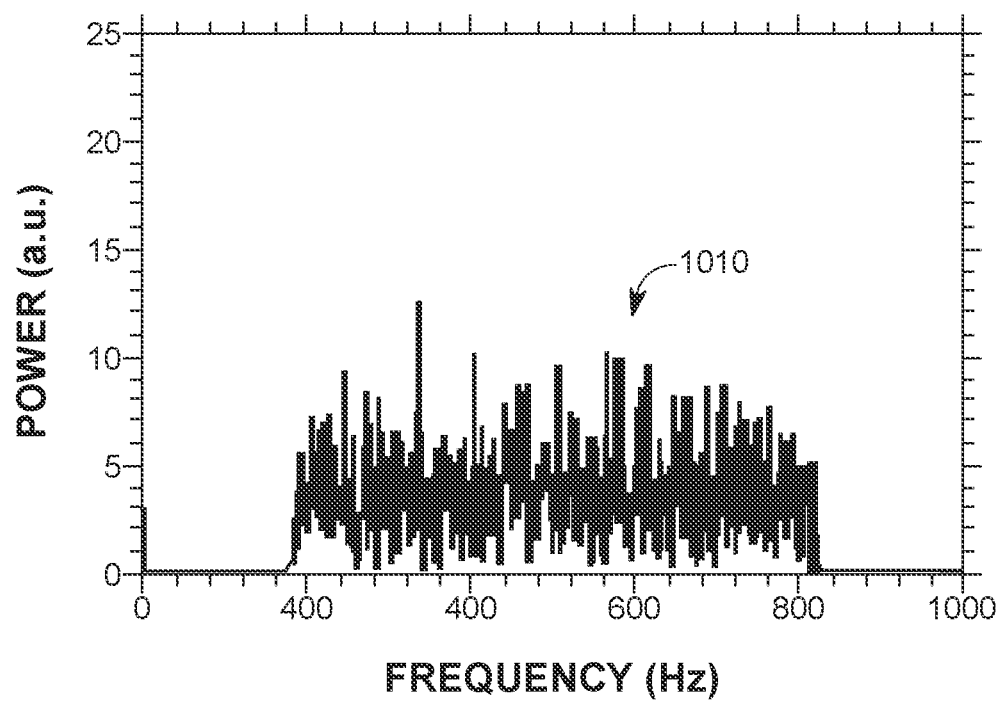

FIGS. 9A and 9B show two representative examples of the time domain signals 900 and 910 recorded with the DAS system 400, for a time of 1 s, after applying the band-pass filter noted above. FIGS. 9C and 9D illustrate the corresponding power spectra 902 and 912, respectively. For comparison purposes, when using the same filtering band, FIG. 10A shows an example for the time domain signal 1000 and FIG. 10B shows the power spectrum 1010 of the background noise recorded by the optical fiber DAS system 400. Again, the larvae sound 900 and 910 and background noise 1000 are recorded under the same experimental conditions, i.e., their strengths can be compared in FIGS. 9A to 10B.

These figures indicate that the larvae signal 900 and 910 is stronger than that of the background noise 1000 in the time domain, but also in the frequency domain (when comparing elements 902, 912, and 1010). Based on these results, the DAS system 400 shows the ability to discover the presence of weevil larvae even if background noise is present. Its reliability can be determined through a statistical analysis, as will be discussed later. Additionally, more advanced signal processing techniques might be required to avoid the instantaneous noises that might produce false alarms through interference with the real larvae signal.

Figure 11:
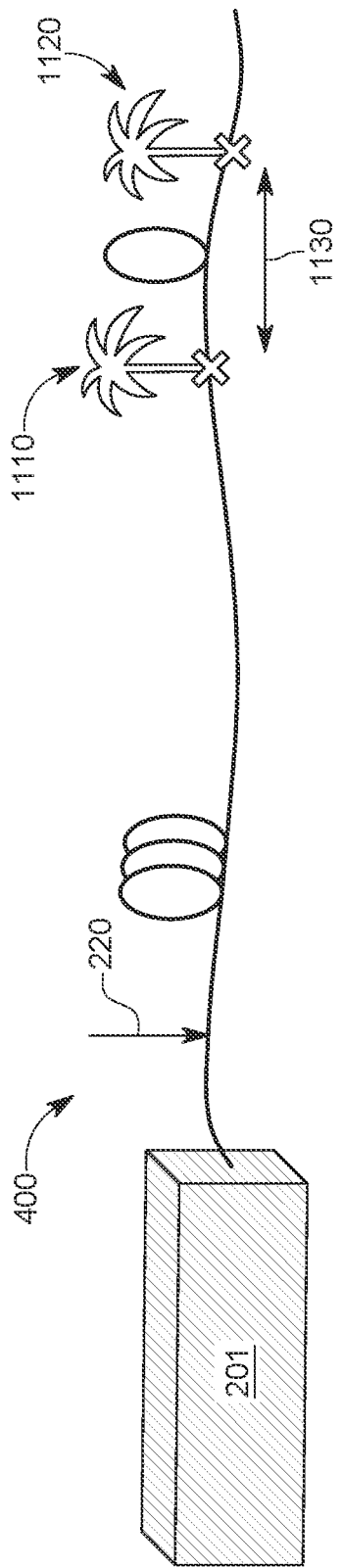
FIG. 11 illustrates a configuration for studying an infected tree and a healthy tree with the DAS system.

Next, an algorithm for determining whether a palm tree is infested or not is discussed. The DAS system 400 is used with a SMF 220 having a length of about 1.1 km length. Near the optical fiber end, a 10 m section is wound around a healthy tree 1110 and another 10 m section is wound around a damaged tree, which is infested with larvae of about 12 days age, as illustrated in FIG. 11. The 10 m section may be replaced with sections having a length between 1 and 20 m. The two trees are well separated in space such that the fiber's length 1130 between them is about 40 m (any distance between 5 m and 100 m may be used). Smaller or larger distances may be used depending on the resolution of the processing equipment. This distance is chosen so that the recording sensor is capable to distinguish the individual signals of the two trees.

Figure 12:
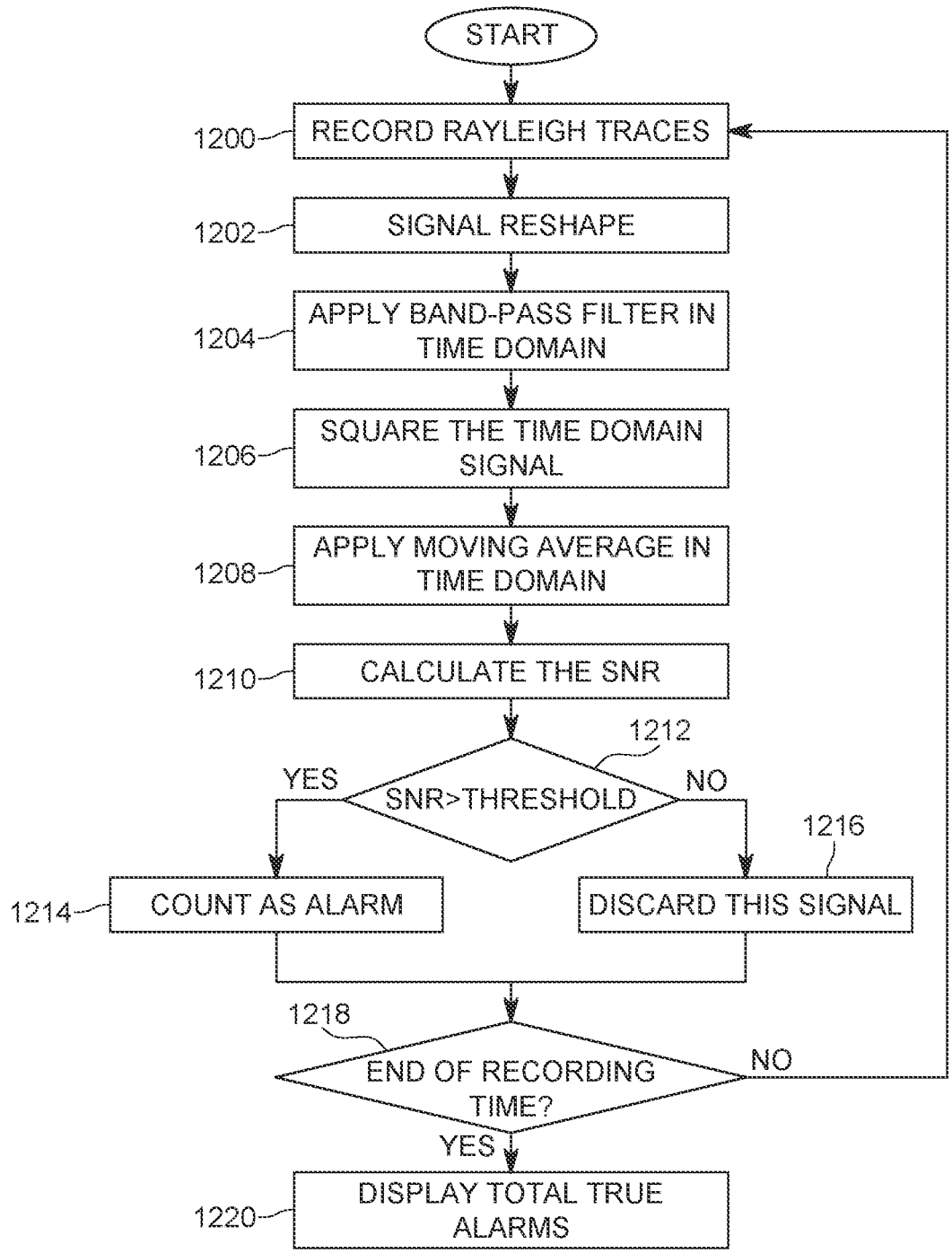
FIG. 12 is a flowchart of a method for determining when a tree is infected based on the DAS system.

The algorithm for detecting the RPW is now discussed with regard to the flowchart of FIG. 12. The method starts in step 1200 with a reading (could be continuous or not) of the Rayleigh traces for a 1 s period. The 1 s period is selected due to the memory constraints associated with the oscilloscope 418 and the computer 211. This time period can be smaller or bigger. In one application, this time period is in the range of minutes, hours, days, etc. In one application, the step 1200 is performed for a given amount of time each day. The given among of time may be between 30-60 minutes. Other time intervals may be used. In step 1202, the continuously recorded Rayleigh traces are reshaped (by known methods and algorithms) into individual ones, such that each trace appears to be the outcome of sending one single pulse through the optical fiber 220. Then, in step 1204, the method applies a band-pass filter in the [200 Hz, 800 Hz] range in the time domain, on the signal of the individual points along the optical fiber. Other values may be used for the band-pass filter depending on the background noise recorded for each location in the farm. The band-pass filter of [200 Hz, 800 Hz] is selected to remove the background noise determined in FIGS. 10A and 10B, which is recorded when also recording the noise produced by the RPW larvae. Because of the noise introduced by the digital filter in step 1204, the first and last 50 ms of the recorded data is omitted, as it is being considered to be corrupted by the filter. The 50 ms value can be modified to be larger of smaller.

Next, for plural points along the optical fiber 220, the method squares in step 1206 the filtered signal received from step 1204, in the time domain, and then the method applies in step 1208, to the squared signal, a moving average with a 100 ms window. The size of the window can be smaller or larger. The moving average means that an average for the squared signal over the 100 ms window is calculated and represented as a point, then the window is moved, maybe, for 1 ms, and a new average is calculated and represented as a new point, an so on until all the squared signals are processed. Both the 100 ms and 1 ms values are exemplary and these values can be increased or decreased as necessary. The 100 ms value has been selected by the inventors based on the observation that the RPW larvae do not eat continuously, but they start and stop, within time intervals less than 100 ms.

In this regard, there are four different scenarios that might impact the results of the moving average step 1208. The first scenario occurs when the system 400 records background noise without any instantaneous time domain noisy spikes. In this case, the result of the moving average is almost of constant amplitude. The second case is when the background noise includes some instantaneous noisy spikes. Since these spikes typically occur within short time periods (i.e., <<100 ms), the moving average results would still have a relatively constant amplitude. The third scenario happens when the signal is captured while the larvae are present and active, i.e., eating. Based on the inventors' observations while analyzing the data, the optical fiber DAS system 400 typically does not record continuous larvae sound within the one second time frame. This might be attributed to that the larvae eating behavior is not continuous, instead they eat in a discrete manner. Another possible reason is because the sound strength produced by the larvae is not constant; therefore, when the sound signal is strong the optical fiber can capture it; otherwise, the sound is weak to disturb the fiber refractive index. In this third scenario, the moving average result consists of hills and valleys. Finally, the last scenario, which rarely occurs, happens when the optical fiber 220 records a larvae sound signal continuously during the one second period with almost the same strength, i.e., the many larvae that have infested the tree do not stop eating and their signal reaches the optical fiber with almost constant strength. In this case, the moving average result is of almost constant high value and it behaves similarly as that result obtained when recording background noise, i.e., a moving average without hills and valleys.

Figure 13:
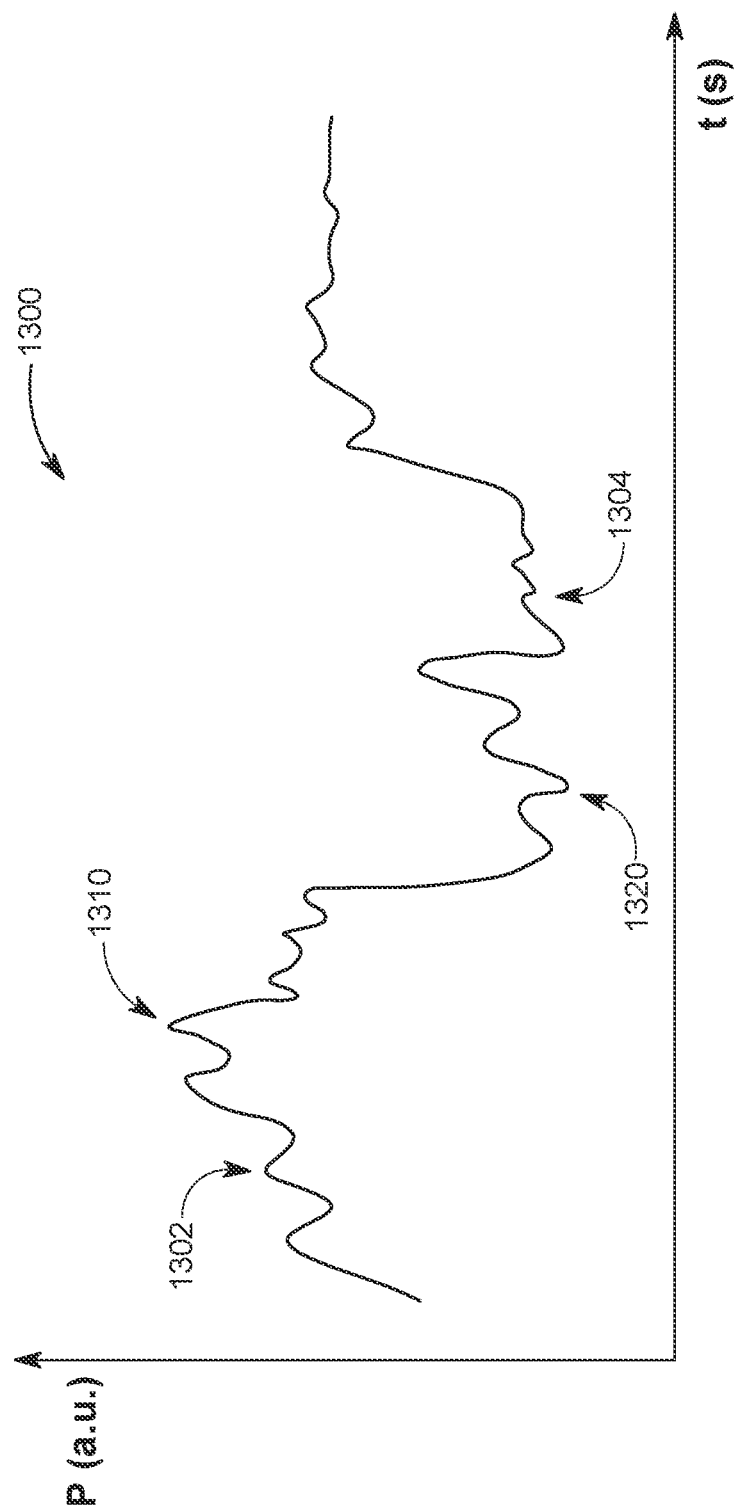
FIG. 13 illustrates a simulated signal and how to calculate a novel signal-to-noise ratio for that signal.
Figure 14A:
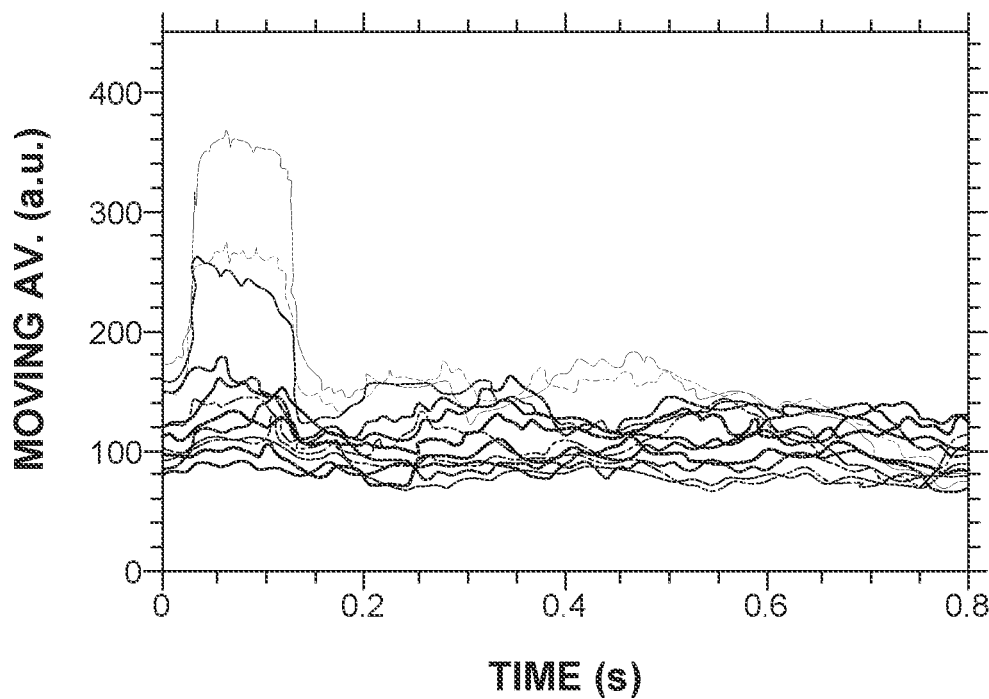
FIGS. 14A to 14D illustrate various processed signals obtained with the DAS system for an infested tree.
Figure 14B:
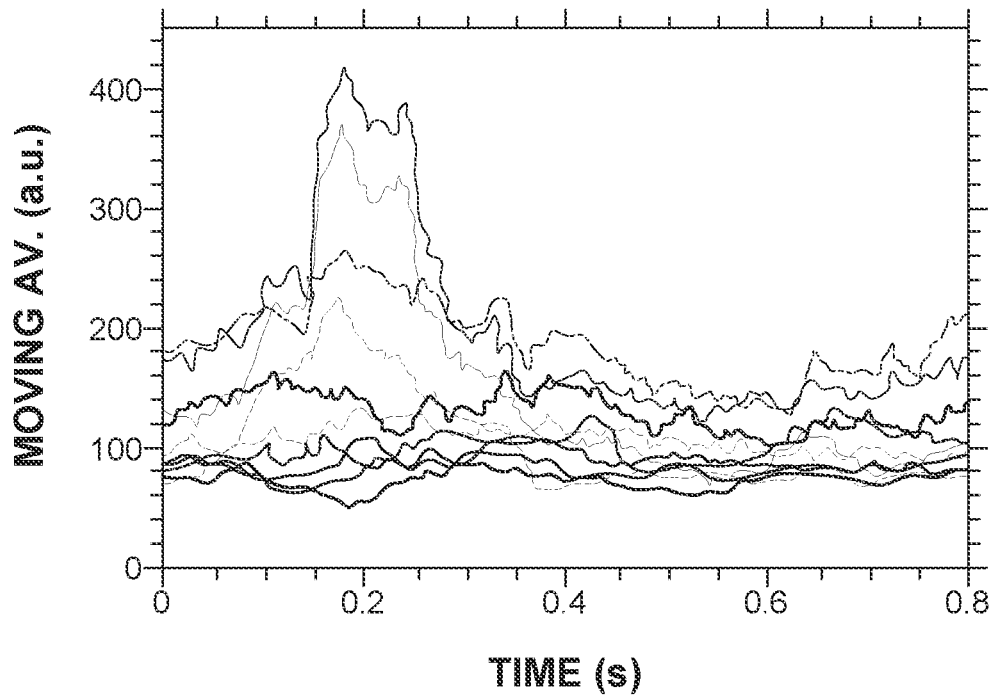
Figure 14C:
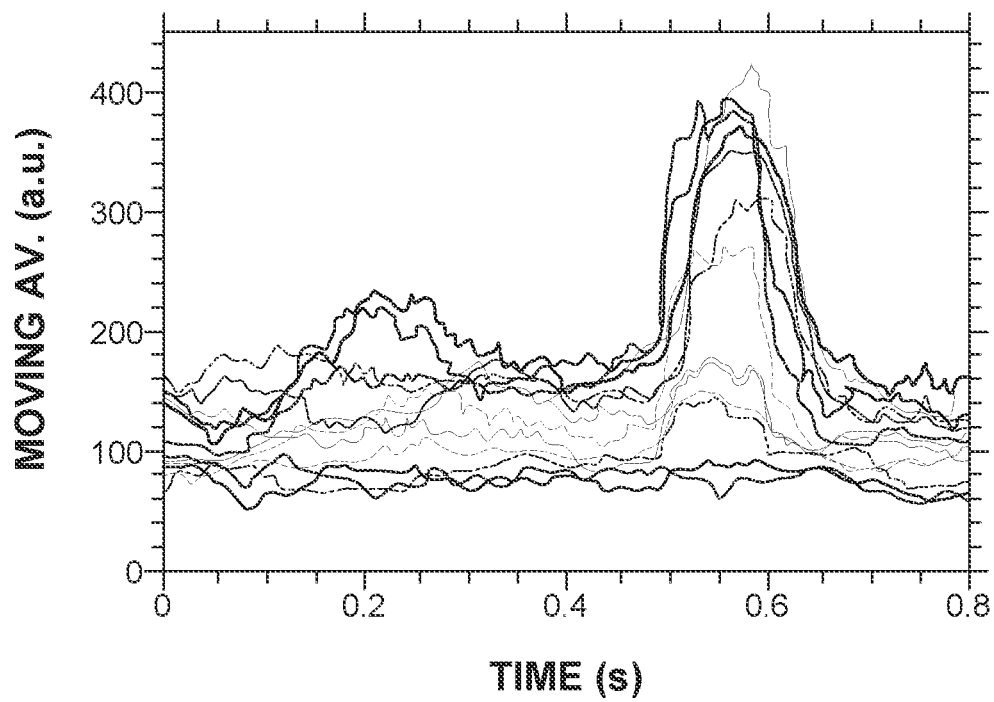
Figure 14D:
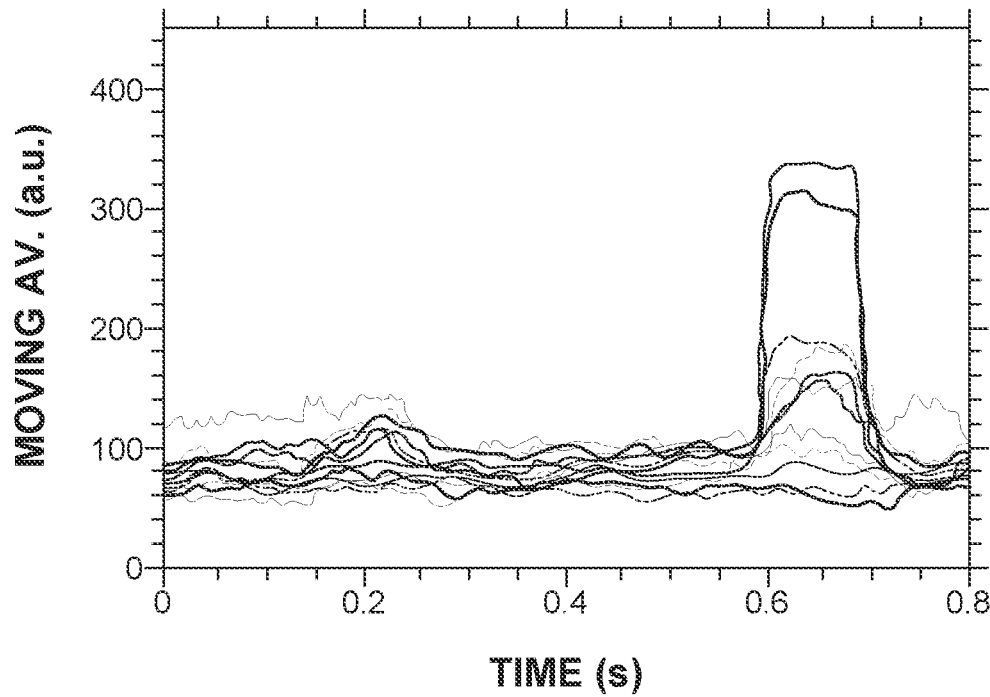
Figure 15A:
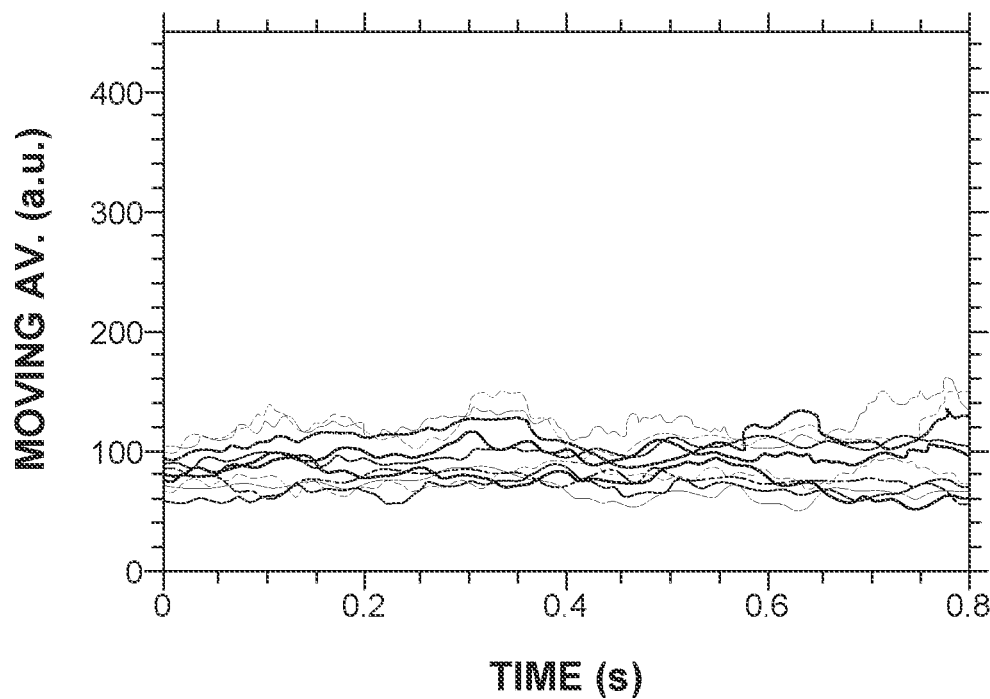
FIGS. 15A to 15D illustrate various processed signals obtained with the DAS system for a healthy tree.
Figure 15B:
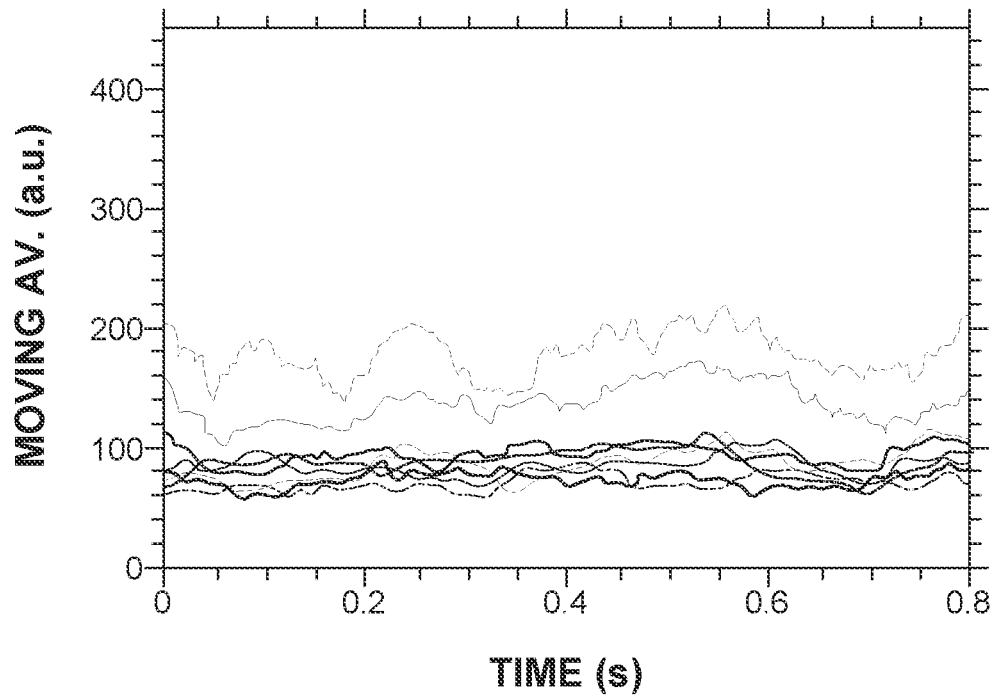
Figure 15C:
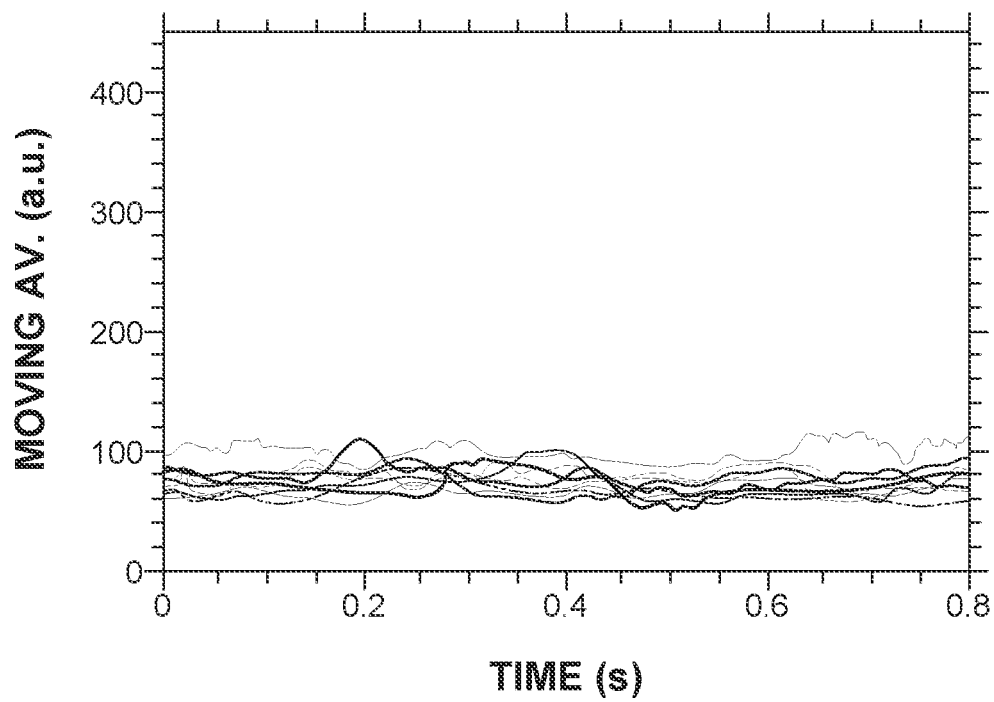
Figure 15D:
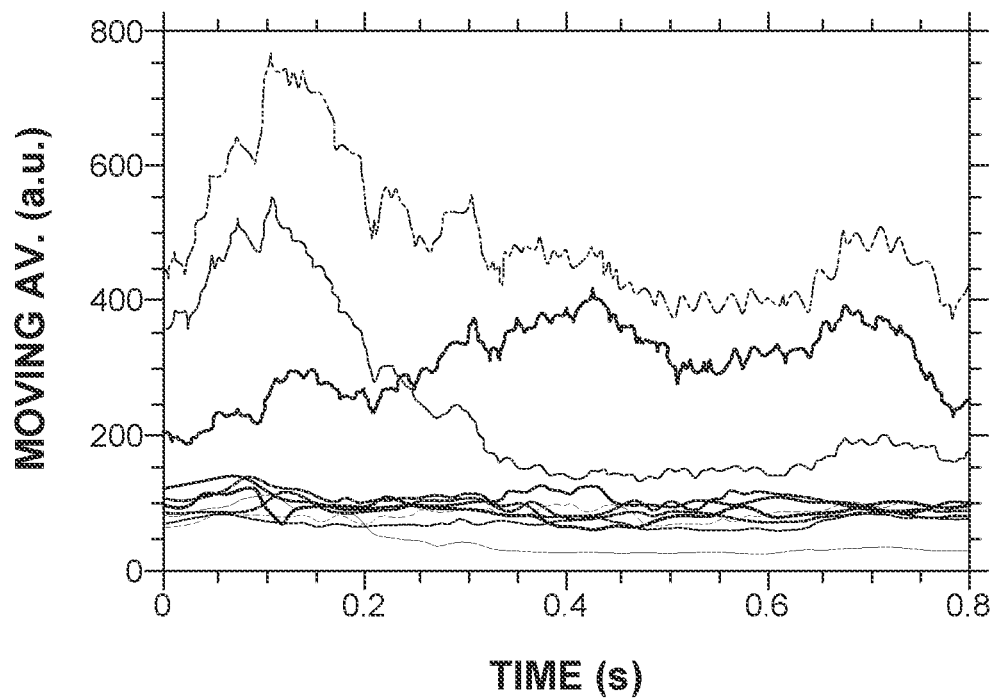

After calculating the moving average for the recording signals in step 1208, the method advances to step 1210, for determining the signal-to-noise ratio (SNR) in the averaged signals. The SNR in the averaged signals it defined herein as being the ratio between (1) the highest-level of the hills to (2) the lowest level of the valleys, where the hills and the valleys are the result of the moving average step. To exemplify this concept, FIG. 13 shows an arbitrary representation of the power 1300 of a signal, having multiple hills 1302 and multiple valleys 1304. Each hill and each valley is a result of a moving average calculation for a given time window, for example, 100 ms. The highest hill is indicated by reference number 1310 while the lowest valley is indicated by reference number 1320. The ratio of these two specific values 1310 and 1320 gives the SNR. Thus, the SNR as defined in this application is different from a generic SNR that is used in the signal processing (which is the ratio between a signal and the noise).

Returning to FIG. 12, if the SNR calculated in step 1210 is determined in step 1212 to be higher than a predetermined threshold value, the method advances to step 1214 and counts this determination as a true alarm of larvae infestation. Otherwise, the method advances to step 1216 and discards the SNR. Next, the method advances to step 1218 where it is checked whether an end of the recoding time has been reached. If the answer is no, the method returns to step 1200 and repeats the procedure discussed above. If the answer is yes, then the method advances to step 1220, where the total number of true alarms for each palm tree that is monitored by the DAS system 400 is calculated and displayed. Based on this number, the person monitoring the farm or the DAS system 400 can decide which palm tree is infected and what action to take to prevent the further spread of the RPW.

FIGS. 14A-14D show four representative examples of the change of the moving average with time for the data collected using the infested tree. For these examples, a 125 MHz oscilloscope sampling rate was used, which means that the system sampled the data every 0.8 m along the optical fiber 220. Each graph in FIGS. 14A to 14D includes 14 curves, one for each spatial point, which adequately covers the 10 m section fiber wound around the tree. One skilled in the art would understand that the 14 curves is a result of the sampling rate of the oscilloscope and the 10 m length of the optical fiber that was placed around the trunk of each tree. If any of these parameters changes, the number of curves changes. Further, the system discussed herein can work with only one curve, or a number of curves less than 14, for example, 10. Further, the 10 m length of the optical fiber provided around the trunk of the palm tree can be increased or decreased.

The SNR in step 1210 may be calculated for all the individual 14 curves and then these maximum values are selected for comparison with the given threshold in step 1212. In this way, there are effectively 14 measurements points for each palm tree. As shown in FIGS. 14A to 14D, the moving average of the infested tree data includes hills and valleys, similar to the simulated data illustrated in FIG. 13. In contrast, FIGS. 15A to 15D show the change of the moving average with time for the signals gathered using the healthy tree. The moving average results for the healthy tree exhibit smooth fluctuations, compared to the infested tree case of FIGS. 14A to 14D. In some rare cases, as that shown in FIG. 15D, the moving average of the healthy tree might include some hills and valleys and the corresponding SNR value may exceed the given threshold in step 1212, which produces a false alarm regarding the tree infestation.

Figure 16A:
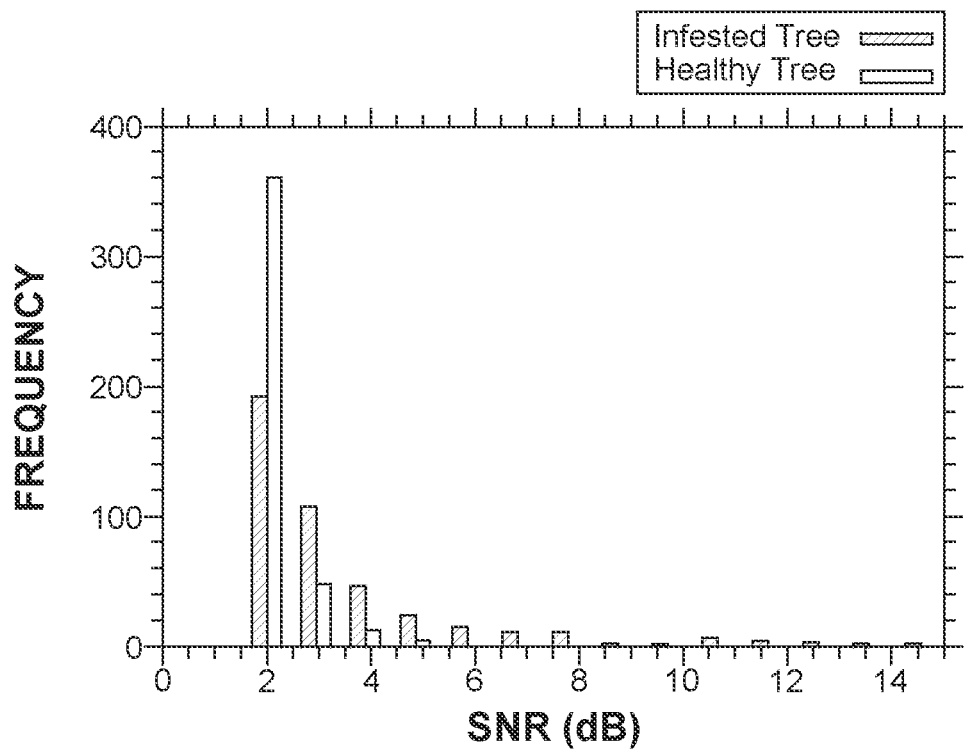
FIGS. 16A and 16B illustrate the alarms obtained with the algorithm of FIG. 12 when using the DAS system for healthy and infested trees.
Figure 16B:
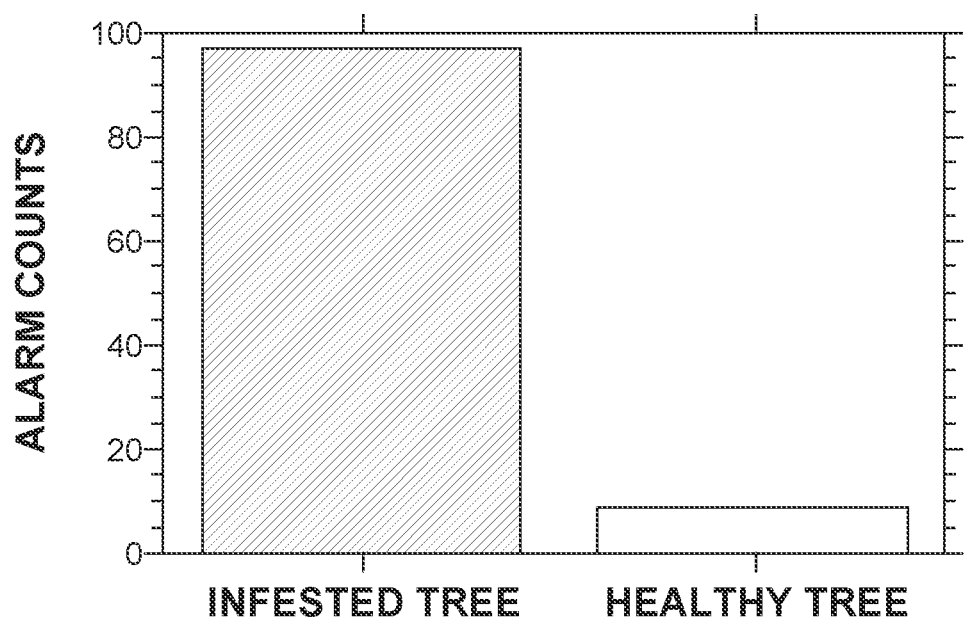
Figure 17:
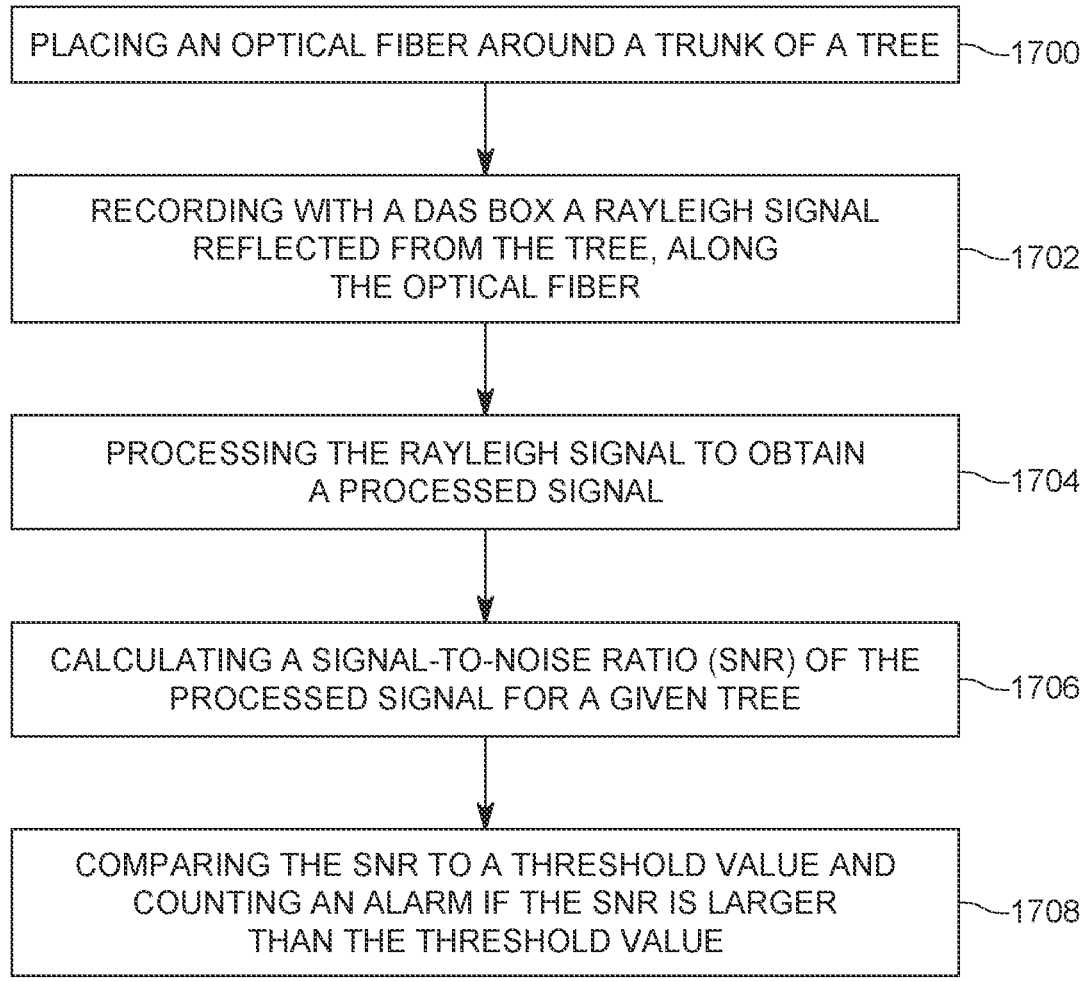
FIG. 17 is a flowchart of another method for determining when a tree is infected based on the DAS system.

For the statistical analysis purpose, the inventors run these measurements and calculations continuously for two hours (any amount of time may be used for these measurements) while calculating the SNR for both the infested and healthy tree. FIG. 16A illustrates the histogram of the SNR values for the infested tree (black bar) and for the healthy tree (white bar) when choosing 1 dB as a bin. Based on the results of this histogram, it is possible to select a certain value (e.g., 4 dB) as the SNR decision threshold to determine whether the tree is infested or healthy. Using the value of substantially 4 dB as the decision threshold value, the DAS system 400 provides 97 infestation alarm counts for the infested tree versus only 9 for the healthy tree, as shown in FIG. 16B. Note that the term "substantially" is used herein as meaning within plus or minus 15% of the actual value of 4 dB. These results confirm the ability of the DAS system 400 to distinguish between infested and healthy trees with a relatively high accuracy. This means that in step 1220, the method may determine if a tree is infested by comparing whether the number of alarms (e.g., 97) for a given time interval (e.g., 2 h) is larger than a given threshold (e.g., 9). Other numbers than the one used herein may be used.

The above embodiments demonstrate the capability for distinguishing between infested and healthy trees using the optical fiber DAS system 400 of 10 m spatial resolution and about 1.1 km fiber length. As known in the art, the sensing range of the optical fiber DAS system 400 can be extended to about 10 km with a 1 m spatial resolution. Assuming the sum of the separation between two consecutive trees and the fiber length wound around each tree is about 10 m, one DAS system 400 with a single optical fiber 220 as illustrated in FIG. 4 would be able to continuously monitor about 1,000 palm trees. Additionally, in order to reduce the monitoring cost per tree, in one embodiment it is possible to combine time-division-multiplexing (TDM) with the DAS system 400. This could be performed via connecting multiple optical fibers to the sensing unit through an optical switch, as illustrated in FIG. 3C.

The signal processing algorithm illustrated in FIG. 12 is capable to identify infested trees and can be generalized for any event count analysis using the optical fiber DAS system 400. The typical SNR definition for an optical fiber DAS is defined as the ratio between the peak-to-peak signal variations to that of the background noise, in the time domain. Following this typical SNR definition, any noisy spike that occurs at a tree location would provide a false infestation alarm. In contrast, the novel SNR definition introduced above significantly mitigates producing such false alarms. The moving average window, 100 ms in this analysis, but other values can be used, can be tuned based on the actual farm that is monitored to even become the entire recording time period. However, as illustrated in FIG. 16B, the decision threshold should be carefully selected based on the used moving average window.

In one embodiment, the detection method for RPW using the optical fiber DAS system 400 is configured to detect the presence of ~12 days old weevil larvae in a palm tree. The method includes a step 1700 of placing the optical fiber 220 around a trunk of a tree, a step 1702 of recording with the DAS box 201 a Rayleigh signal reflected from the tree, along the optical fiber 220, a step 1704 of processing the Rayleigh signal to obtain a processed signal, a step 1706 of calculating a signal-to-noise ratio SNR of the processed signal for a given tree, and a step of comparing the SNR to a threshold value and counting an alarm if the SNR is larger than the threshold value. The SNR is defined as a ratio between (1) a maximum value of a signal and a minimum value of the processed signal.

The method may further include a step of applying a band-pass filter to the processed signal to obtain a squared band-passed signal, from which a noise associated with the tree is removed. In one application, the band-pass filter removes frequencies between 200 and 800 Hz. The method may further include a step of squaring the band-passed signal to obtained a squared signal, and a step of applying a moving average, in the time domain, to the squared signal, to obtain the processed signal. Further, the method may include reshaping the Rayleigh signal. The threshold value is selected to be substantially 4 dB, the tree is a red palm, and the tree infestation is associated with a larva of the red palm weevils.

In one application, the optical fiber is connected to the DAS box, the optical fiber has a length of over 1 km, and plural parts of the optical fiber are wounded around plural trunks of red palm trees in a farm. A length of the optical fiber that connects wounded regions of the optical fiber is between 5 and 100 m, and the plural parts that are wounded around the plural trunks each has a length between 1 and 20 m. The step of calculating may further include receiving plural processed signals for a given tree, for a given time window, wherein each processes signal corresponds to another location on the given tree, and calculating the SNR for each processed signal. The method may further include comparing plural SNR to the threshold value for the different locations along the given tree and generating corresponding alarms.

The system 400 for determining tree infestation may be configured to include the optical fiber 220, which is configured to be placed around a trunk of a tree, the DAS box 201 connected to the optical fiber 220 and configured to record a Rayleigh signal reflected from the tree, along the optical fiber 220, and the processor 211. The processor 211 may be configured to process 1704 the Rayleigh signal to obtain a processed signal, calculate 1706 a signal-to-noise ratio (SNR) of the processed signal for a given tree, and compare 1708 the SNR to a threshold value and counting an alarm if the SNR is larger than the threshold value. The SNR is defined as a ratio between (1) a maximum value of a signal and a minimum value of the processed signal.

The system may further include a band-pass filter that filters the processed signal to obtain a squared band-passed signal, from which a noise associated with the tree is removed. In one application, the band-pass filter removes frequencies between 200 and 800 Hz. The processor may be further configured to square the band-passed signal to obtained a squared signal, and apply a moving average, in the time domain, to the squared signal, to obtain the processed signal. The threshold value is selected to be substantially 4 dB, the tree is a red palm, and the tree infestation is associated with a larva of the red palm weevils.

In one embodiment, the optical fiber has a length of over 1 km, and plural parts of the optical fiber are wounded around plural trunks of red palm trees in a farm. A length of the optical fiber that connects wounded regions of the optical fiber is between 5 and 100 m, and the plural parts that are wounded around the plural trunks each has a length between 1 and 20 m. The processor may be further configured to receive plural processed signals for a given tree, for a given time window, wherein each processes signal corresponds to another location on the given tree, and calculate the SNR for each processed signal. The processor may be further configured to compare plural SNR to the threshold value for the different locations along the given tree and generating corresponding alarms.

The disclosed embodiments provide an optical DAS system for monitoring tree infestation and a method for determining the presence of the RPW larvae in the tree. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

References

[1] Rach, M. M. et al. On the design of a bioacoustic sensor for the early detection of the red palm weevil. *Sensors* (Switzerland) 13, 1706-1729 (2013).

[2]. Gutiérrez, A., Ruiz, V., Moltó, E., Tapia, G. & del Mar Téllez, M. Development of a bioacoustic sensor for the early detection of Red Palm Weevil (*Rhynchophorus ferrugineus* Olivier). *Crop Prot.* 29, 671-676 (2010).

[3]. Siriwardena, K. A. P. et al. Portable acoustic device for detection of coconut palms infested by *Rynchophorus ferrugineus* (Coleoptera: Curculionidae). *Crop Prot.* 29, 25-29 (2010).

[4]. Hussein, W. B., Hussein, M. A. & Becker, T. Detection of the red palm weevil *Rhynchophorus ferrugineus* using its bioacoustics features. *Bioacoustics* 19, 177-194 (2010).

[5]. Mankin, R. W. Recent Developments in the use of Acoustic Sensors and Signal Processing Tools to Target Early Infestations of Red Palm Weevil in Agricultural Environments 1. *Florida Entomol.* 94, 761-765 (2012).

[6] Mao, Y., Ashry, I., Ng, T. K. & Ooi, B. S. Towards Early Detection of Red Palm Weevil Using Optical Fiber Distributed Acoustic Sensor. in W2A.15 (2019). doi:10.1364/ofc.2019.w2a.15.

[7] Yuelan Lu, Tao Zhu, Liang Chen & Xiaoyi Bao. Distributed Vibration Sensor Based on Coherent Detection of Phase-OTDR. *J. Light. Technol.* 28, 3243-3249 (2010).

What is claimed is:

1. A method for determining tree infestation, the method comprising:
   placing an optical fiber around a trunk of a tree;
   recording with a distributed acoustic sensor (DAS) box a Rayleigh signal reflected from the tree, along the optical fiber;
   processing the Rayleigh signal to obtain a processed signal;
   calculating a signal-to-noise ratio (SNR) of the processed signal for the tree; and
   comparing the SNR to a threshold value and counting an alarm if the SNR is larger than the threshold value, wherein the SNR is defined as a ratio between (1) a maximum value of the processed signal and (2) a minimum value of the processed signal.

2. The method of claim 1, further comprising:
   applying a band-pass filter to the processed signal to obtain a squared band-passed signal, from which a noise associated with the tree is removed.

3. The method of claim 2, wherein the band-pass filter removes frequencies between 200 and 800 Hz.

4. The method of claim 2, further comprising:
   squaring the band-passed signal to obtained a squared signal; and
   applying a moving average, in the time domain, to the squared signal, to obtain the processed signal.

5. The method of claim 1, wherein the threshold value is selected to be substantially 4 dB, the tree is a red palm, and the tree infestation is associated with a larva of the red palm weevils.

6. The method of claim 1, wherein the optical fiber is connected to the DAS box, the optical fiber has a length of over 1 km, and plural parts of the optical fiber are wounded around plural trunks of red palm trees.

7. The method of claim 6, wherein a length of the optical fiber that connects wounded regions of the optical fiber is between 5 and 100 m, and the plural parts that are wounded around the plural trunks each has a length between 1 and 20 m.

8. The method of claim 1, wherein the step of calculating further comprises:
receiving plural processed signals for the tree, for a given time window, wherein each processed signal corresponds to another location on the tree;
calculating the SNR for each processed signal; and
comparing plural SNR to the threshold value for the different locations along the tree and generating corresponding alarms.

9. The method of claim 1, wherein the optical fiber is surrounded by a shield layer to form an optical fiber assembly, and a first portion of the optical fiber assembly is located underground, and a second portion of the optical fiber layer is located above ground.

10. The method of claim 1, further comprising:
applying time multiplexing to optical signals received from plural optical fibers.

11. A system for determining tree infestation, the system comprising:
an optical fiber that is configured to be placed around a trunk of a tree;
a distributed acoustic sensor (DAS) box connected to the optical fiber and configured to record a Rayleigh signal reflected from the tree, along the optical fiber; and
a processor configured to,
process the Rayleigh signal to obtain a processed signal,
calculate a signal-to-noise ratio (SNR) of the processed signal for the tree, and
compare the SNR to a threshold value and count an alarm if the SNR is larger than the threshold value,
wherein the SNR is defined as a ratio between (1) a maximum value of the signal and (2) a minimum value of the processed signal.

12. The system of claim 11, further comprising:
a band-pass filter that filters the processed signal to obtain a band-passed signal, from which a noise associated with the tree is removed,
wherein the band-pass filter removes frequencies between 200 and 800 Hz.

13. The system of claim 12, wherein the processor is further configured to:
square the band-passed signal to obtained a squared signal; and
apply a moving average, in the time domain, to the squared signal, to obtain the processed signal.

14. The system of claim 12, wherein the optical fiber is surrounded by a shield layer to form an optical fiber assembly, and a first portion of the optical fiber assembly is located underground, and a second portion of the optical fiber layer is located above ground.

15. The system of claim 14, wherein the first portion is rigid and the second portion is flexible.

16. The system of claim 11, wherein the threshold value is selected to be substantially 4 dB, the tree is a red palm, and the tree infestation is associated with a larva of the red palm weevils.

17. The system of claim 11, wherein the optical fiber has a length of over 1 km, and plural parts of the optical fiber are wounded around plural trunks of red palm trees.

18. The system of claim 17, wherein a length of the optical fiber that connects wounded regions of the optical fiber is between 5 and 100 m, and the plural parts that are wounded around the plural trunks each has a length between 1 and 20 m.

19. The system of claim 18, wherein the processor is further configured to:
receive plural processed signals for the tree, for a given time window, wherein each processes signal corresponds to another location on the tree;
calculate the SNR for each processed signal; and
compare plural SNR to the threshold value for the different locations along the tree and generate corresponding alarms.

20. A method for determining tree infestation in red palm trees, the method comprising:
recording with a distributed acoustic sensor (DAS) box a Rayleigh signal reflected from the red palm trees, wherein the Rayleigh signals is received from an optical fiber wounded around trunks of the red palm trees;
processing the Rayleigh signal to obtain a processed signal;
calculating a signal-to-noise ratio (SNR) of the processed signal for a given tree; and
comparing the SNR to a threshold value and counting an alarm if the SNR is larger than the threshold value,
wherein the SNR is defined as a ratio between (1) a maximum value of the signal and (2) a minimum value of the processed signal.

* * * * *